US005558867A

United States Patent [19]

Sakaguchi et al.

[11] Patent Number: 5,558,867

[45] Date of Patent: Sep. 24, 1996

[54] RECOMBINANT MAREK'S DISEASE VIRUS, PROCESS FOR PREPARING THE SAME AND VACCINE CONTAINING THE SAME

[75] Inventors: Masashi Sakaguchi; Michitaka Yamamoto, both of Kikuchi-gun, Japan

[73] Assignee: Juridical Foundation The Chemo-Sero-Therapeutic Research Institute, Kumamoto, Japan

[21] Appl. No.: 272,513

[22] Filed: Jul. 7, 1994

Related U.S. Application Data

[63] Continuation of Ser. No. 910,554, Jul. 8, 1992, abandoned.

[30] Foreign Application Priority Data

Jul. 9, 1991 [JP] Japan .................................... 3-195703

[51] Int. Cl.$^6$ ........................ A61K 39/295; A61K 39/17; A61K 39/255; C12N 7/01; C12N 15/00

[52] U.S. Cl. .................................... 424/199.1; 424/229.1; 424/214.1; 435/235.1; 435/320.1; 435/172.3; 935/32; 935/65

[58] Field of Search ......................... 435/69.1, 91, 177.3, 435/235.1, 240.2, 320.1; 530/300, 350; 424/88, 89, 199.1, 214.1, 229.1; 536/23.1, 23.5; 935/10, 32, 57, 65

[56] References Cited

U.S. PATENT DOCUMENTS

| | | | |
|---|---|---|---|
| 5,138,033 | 8/1992 | Velicer et al. | 530/395 |
| 5,171,677 | 12/1992 | Sakaguchi et al. | 435/172.3 |
| 5,231,023 | 7/1993 | Morgan | 435/240.2 |
| 5,470,734 | 11/1995 | Sondermeijer et al. | 424/229.1 |

FOREIGN PATENT DOCUMENTS

| | | | |
|---|---|---|---|
| 0334530 | 9/1989 | European Pat. Off. | C12N 15/00 |
| 361182 | 4/1990 | European Pat. Off. | C12N 15/86 |
| 0361182 | 4/1990 | European Pat. Off. | C12N 15/86 |
| 8912684 | 12/1989 | WIPO | C12N 15/00 |
| 9002802 | 3/1990 | WIPO | C12N 15/30 |
| 9203547 | 3/1992 | WIPO | C12N 15/00 |

OTHER PUBLICATIONS

Ogawa et al Vaccine vol. 8 pp. 486–490 (1990).

Taylor et al J. Virol. vol. 64 pp. 1441–1450 (1990).

Sakaguchi et al Virus Genes vol. 6 pp. 365–378 (1992).

Cantello et al., "Isolation of a Marek's Disease Virus (MDV) Recombinant Containing the LacZ Gene of *Escherichia coli* Stably Inserted within the MDV US2 Gene," J. of Virology, vol. 65, No. 3 (1991) pp. 1584–1588.

Igarashi et al., "Restriction Enzyme Map of Herpesvirus of Turkey DNA and Its Collinear Relationship with Marek's Disease Virus DNA," Virology, vol. 157, No. 2 (1987), pp. 351–358.

Fukuchi et al., "The Structure of Marek Disease Virus DNA: The Presence of Unique Expansion in Nonpathogenic Viral DNA," Proc. Natl. Acad. Sci. USA, vol. 82, No. 1, (1985), pp. 751–754.

*Primary Examiner*—Mary E. Mosher
*Attorney, Agent, or Firm*—Foley & Lardner

[57] ABSTRACT

A recombinant Marek's disease virus produced by the mutation of a Marek's disease virus with a plasmid wherein said plasmid comprises (1) a gene fragment derived from the Us region or inverted repeat sequences adjacent to both ends of said Us region of a Marek's disease virus genome and (2) an exogenous gene expression cassette incorporated in said gene fragment, said cassette comprising an exogenous gene bound downstream of a promoter derived from an animal cell or an animal virus, a process for preparing the same, a multivalent live vaccine for birds comprising the same, and a vector for administration of a physiologically active substance to birds which comprises the same.

7 Claims, 14 Drawing Sheets

FIG. 12A

```
GAATTCCTTC CTTTAAAATG AAAGATGTCC AGGTAGACGA TGCGGGATTG TATGTGGTTG   60
TGGCTTTATA TAATGGACGT CCAAGTGCAT GGACTTACAT TTATTTGTCA ACCGGTGAAA  120
CACTATCNTT AAATGTGGAA TGTATATGAA AACTACCACA AGCCGGGATT TGGGTATAAA  180
TCATTTCTAC AGAACAGTAG TATCATCGAC GAAAATGAGG CTAGCGATTG GTCCAGCTCG  240
TCCATTAAAC GGAGAAATAA TGGTACTATC CTTTATGATA TTTTACTCAC ATCGCTATCA  300
ATTGGGGCGA TTATTATCGT CATAGTAGGG GGTGTTTGTA TTGCCATATT AATTAGGCGT  360
AGGAGACGAC GTCGCACGCG GGGGTTATTC GATGAATATC CCAAATATAT GACGCTACCA  420
GGAAACGATC TGGGGGGCAT GAATGTTCCG TATGATAATG CATGCTCTGG TAACCAAGTT  480
GAATATTATC AAGAAAAGTC GGATAAAATG AAAAGAATGG GTTCGGGTTA TACCGCTTGG  540
CTAAAAAATG ATATNCCGAA ATTNGNAACC CCTAGATTTA ATCCCACTGA TATGNACANA  600
TTTAAACTTA ATGGGATATA GTATATGGAC GTCTATATGA CGAGAGTAAA TAAACTGACA  660
CTGCAAATGA AGCTGATCTA TATTGTGCTT TATATTGGGA CAAACCACTC GCACAAGCTC  720
ATTCAACACA TCCACTCTTG GACAGCTTCA TGTTAAAATA AACTGTAAAT CATTCAATGA  780
TAATGGGAGA AGAATGTGAG CAAGGATCCA TGGTGTCTGC TTTTTATAGT ATCTACCGCA  840
          US←┐┌→ TRs
ATGCTACATA TAAAATAAAA ATATACCTCT ACCCAAAAAT GGGCGGTATG AGATGCACGG  900
GGAAAATACG CAGCTGTTCT CATATCCCCT GAACCGTACT CTTTTTCCCC TCTCCGCCCC  960
GCGGACCCCG AGGCCTCGTG GGGCACCTAT TTGCGCGGAG GAAGGCACGG TTCCTTTTTT 1020
TTTTGGGGGG GGGGGACCCA TCTGCGTAGA NAAAGGCACG GTTCCTCTTT TTTTTTTCCT 1080
ACAACATCTC GTTTGCATAT GCAAGCTCTG AGAACTTCCC TCTACCTCAA AGCGCCGTAG 1140
GGAACTGAGG TCTAATATTC AATCCTAGGC CACTCGCCAA TATAAGAGGG ACTTCCCCCC 1200
GCCTATAGAG AGAGGCAGCC CGAAAATGGA GCAGTGTAAA GCAGTACATG GGTGGTGGTA 1260
TGAAACTTGC GAATCGGGCT GTAACGGGGC AAGGCTTGAC TGAGGGGACC ATAGTATGTA 1320
TAGGCNAAAG GCGGGGCTTC GGTTGTANGC GGTTAGGAGT CCCCTCAGGA TACAGTAGTT 1380
GCGCTTTTGC ATAGGGAGGG GGAAATGTAG TCAAATAGAG CCAGAGGCAA CTTGAATAGC 1440
CTAAAGACCA AATAAGGAAA AAGCAAGACA TTCCATATGC TCATTGGTGG CGACTAGATA 1500
AGGAAGGAAT GACGCAAGGA CATATGGGCG TAGACGAAGC TATGTACGAT TATATAAGCT 1560
GTTGCCACCA TCAAAATAAA ACGCCATTTT ACCATTCACC ACATTGGTGT GCACCTGGGT 1620
```

FIG. 12B

AGATGGACAG ACCGTTGAGT CCCTAACGAT TGCGAACACC TGAATGAAGC AGAAGGCTTC 1680

ATTAATGTAG TCAAATAGAG CCAGAGGCAA CTTGAATAGC CTAAAGACCA AATAAGGAAA 1740

AAGCAAGACA TTCCATATGC TCATTGGTGG CGACTAGATA AGGAAGGAAT GACGCAAGGA 1800

CATATGGGCG TAGACGAAGC TATGTACGAT TATATAAGCT GTTCCACCAT CAAATAAACG 1860

CCATTTTACC ATTCACCACA TTGGTGTGCA CCTGGGTAGA TGGACAGACC GTTGAGTCCC 1920

TAACGATTGC GAACACCTGA ATGAAGGAGA AGGCCTCATT AATGTAGTCA AATAGAGCCA 1980

GAGGCAACTT GAATAGCCTA AAGACCAAAT AAGGGAAAAG CAAGACATTC CATATGCTCA 2040

TTGGTGGCGA CTAGATAAGG AAGGAATGAC GCAAGGACAT ATGGGCGTAG ACGAAGCTAT 2100

GTACGATTAT ATAAGCTGTT GCCACCATCA AATAAACGCC ATTTTACCAT TCACCACATT 2160

GGTGTGCACC TGGGTAGATG GACAGACCGN TGAGTCCCTN ACGATTGCGN ACACCTNAAT 2220

GAAGNNGAAG GCCTCATTAA TGNAGTCAAA TAGAGCCAGA GGCTAACTTG AATAGCCTAA 2280

AGGACCAAAT AAGGAAAAAG CAAGACATTC CATATGCTCA TTGGTGGCGA CTAGATAAGG 2340

AAGGAATGAC GCAAGGACAT ATGGGCGTAG ACGAAGCTAT GTACGATTAT ATAAGCTAAA 2400

CCCAGGAGAC ACGCTGTGGT TAGCTCGTCG ATTCAGTATC CCCCCCNAAN GGCCCCCCCT 2460

TTTTNGGCCC CNGGTTTNCC NNAANCNTTG NCCAAAAANC CTAGCCCAAA AGCNNCGTAA 2520

NNCTTGGGAT NNTAAAAAAA ANGGAGAACN CGTAAGGCCA AAAAANCTAT TTTAATGGGT 2580

CCCCGACAAA NATAAACACA CTCCCCCCTC CCCCTTNCCC CTGTTCAAGT CAGNAAACCC 2640

GTCGNAAGAT TAATTCTCAA AATCCCAATN CGGCGAGCAT GTAAGACCCC GGCCAATCGT 2700

ACAGAACCCC GAGTTTTGTT TACTTGCAGA TATGCACCGC CCTTCCTTGA CGTGNCAAAC 2760

AAACTAAGCT GTGTTTATAT AAAACGGCAC CCNACCCATA TACTCGTATA CTTGTACGAA 2820

CCAGTGGTTT TTTTATGTGG GGGAGGGAGA AGGACAAATT AAAACATTGN ACTTGCCTGG 2880

GCTACAATTC CCTTTTGGCT CGAGCTATGT CGGAGAGTNC CGGTGGACCC GNGGTTGTGC 2940

TTTGGGCTGA AGGAANTCGA GNTNGGTACC CGGGGANCCT CTAGAGTCGA CCCTGAAAGC 3000

TGTTGCCTTT TTGTTGTATA TGAAGATATT TAATGTGGCG TTGAGCCTAA TGAGAGGAGA

ACGTGTTTGA ACACTGGAGA CGAGCGCCGT GTAAGATTAA AACATATTGG AGAGGTATGG

↓ BalI site

CCATGTGGTC TCTACGGCGC AAATCTAGCA GGAGTGTGCA ACTCCGGGTA GATTCTCCAA

AAGAACAGAG TTATGATATA CTTTCTGCCG GCGGGGAACA TGTTGCGCTA TTGCCTAAAT

CTGTACGCAG TCTAGCCAGG ACCATATTAA CCGCCGCTAC GATCTCCCAG GCTGCTATGA

AAGCTGGAAA ACCACCATCG TCTCGTTTGT GGGGTGAGAT ATTCGACAGA ATGACTGTCA

CGCTTAACGA ATATGATATT TCTGCTTCGC CATTCCACCC GACAGACCCG ACGAGAAAAA

TTGTAGGCCG GGCTTTACGG TGTATTGAAC GTGCTCCTCT TACACACGAA GAAATGGACA

CTCGGTTTAC TATCATGATG TATTGGTGTT GTCTTGGACA TGCTGGATAC TGTACTGTTT

CGCGCTTATA TGAGAAGAAT GTCCGTCTTA TGGACATAGT AGGTTCGGCA ACGGGCTGTG

GAATAAGTCC ACTCCCCGAA ATAGAGTCTT ATTGGAAACC TTTATGTCGT GCCGTCGCTA

CTAAGGGGAA TGCAGCAATC GGTGATGATG CTGAATTGGC ACATTATCTG ACAAATCTTC

GGGAATCGCC AACAGGAGAC GGGGAATCCT ACTTATAACT AATCGCACAA TTATTAATAG

GATTTTAGGA AAAACTGCTA CTAACGTTGT TTAAATAATA AAATTTTATT TTCAATAAGG

CATTACAGTG TTGTCATGAT TGTATGTATT ATATGGGGTA TGCATGAGGA TTACTTCGAT

RECOMBINANT MAREK'S DISEASE VIRUS, PROCESS FOR PREPARING THE SAME AND VACCINE CONTAINING THE SAME

This application is a continuation of U.S. application Ser. No. 07/910,554 filed Jul. 8, 1992, now abandoned.

The present invention relates to a novel virus vector which is capable of expressing an exogenous gene product in a chicken cell or in the body of chicken and a process for preparing the same. The present invention further relates to a construction of a recombinant Marek's disease virus for administration of a physiologically active substance (e.g. a hormone, etc.) into a living body and a multivalent live vaccine for chicken containing the same, which are prepared by employing the vector as set forth above.

TECHNICAL BACKGROUND AND PRIOR ART

In the field of modern poultry farming, prevention of diseases by vaccination is a major means for sanitation regardless of a kind of chicks, i.e. a chick for breeding, a chick for laying eggs or a chick for meat. The vaccination, however, has to be done so frequently that personnel expenses become much higher to cause an economical disadvantage for a poultry farmer. In order to avoid this disadvantage, one can contemplate to simply mix several known vaccines. However, there is a problem that an interference occurs between viruses in case of a mixture of live vaccines and there is also a limitation in mixing amount in case of a mixture of inactivated vaccines. In addition, in case of a mixture of a live vaccine and an inactivated vaccine, there is observed a titer decrease due to an adsorption of a live vaccine antigen to a gel (adjuvant).

Recently, taking into account the above situations, alternative method has been attempted to employ a virus vector, i.e. multiple genes of vaccine antigens are incorporated into a single virus to prepare a multivalent live vaccine. This method makes it possible to prepare a multivalent live vaccine without inducing the interference between viruses or the increase of inoculation amount in case of the mixture of inactivated vaccines as mentioned above.

Hitherto, a research on the use of a virus as a vector has already been conducted in the preparation of vaccines for various viruses such as vaccinia virus, adenovirus, herpes simplex virus, retrovirus, and the like, and Hepatitis B surface antigen (HBs antigen) or glyco-proteins of rabies virus or varicella zoster virus have successfully been expressed in vitro. However, some of these viruses (other than vaccinia virus) are a virus having an oncogencity and hence the administration of these viruses to human or animals is restricted and not practical in viewpoint of safety. In addition, even if the virus itself is safe, it cannot be used effectively as a virus vector for birds, at which the present invention is aimed, since the birds to be inoculated are not an original host of the virus.

Besides, use of avian poxvirus (e.g. chick fowlpox virus) as a vector has been suggested and the virus has already been studied for use as a virus vector. It is reported that an exogenous gene can be incorporated into the virus DNA [Saeki et al., Abstract of the 35th Meeting of Japan Virology Society, page 209 (1987)]. However, in the modern poultry field, immune against fowlpox lasts for only short period of time, and hence, several inoculations of a vaccine virus (attenuated fowlpox virus or pigeon pox virus) are usually required during the breeding of chick. Consequently, when the poxvirus is used as the virus vector, a frequent vaccination is still required even though a virus vector wherein plural antigens are incorporated is prepared and used as a vaccine. In addition, in case of a poxvirus vector, it is known that the growth of poxvirus itself is greatly inhibited by a maternal antibody against the poxvirus and hence a sufficient immune response against the inserted antigens cannot be obtained.

Marek's disease is a malignant tumor whose outbreak can be prevented only by vaccination. The prevention mechanism is considered that when the host birds such as chick is permanently infected with the vaccine virus, humoral and cell-mediated immunities against Marek's disease virus are induced and maintained through life of the host, and thereby tumorigenesis by virulent virus is suppressed. This virus vaccine is usually administered in the form of live cells infected with the virus and characterized by that it can be administered to a new-born chick since the virus propagates via the cell-to-cell infection and hardly affected by the maternal antibody.

In consideration of the above-mentioned characteristics of the Marek's disease virus, in recent years, a multivalent vaccine has been developed using the Marek's disease virus as a vector. In order to prepare the multivalent live vaccine in which Marek's disease virus, the virus having much more excellent properties than those of other virus vectors, is utilized as a vector, it is necessary to find out the site suitable for incorporation of an exogenous gene or the removable region on the Marek's disease virus DNA.

Hitherto, the thymidine kinase (TK) gene and the gA gene on the Marek's disease virus DNA have been studies as the site for incorporation of an exogenous gene. However, it has been reported that the loss of the thymidine kinase activity due to mutation in the TK gene reduces a viral growth [P. Bandyopadyay et al. (1987), 12th INTERNATIONAL HERPESVIRUS WORKSHOP] and a recombinant virus has not been reported wherein an exogenous gene is incorporated into the TK gene. As to the gA gene, it has been reported that a recombinant virus wherein the LacZ gene is incorporated into the gA gene is unstable and cannot be purified [Kato Atsushi et al. (1991), 111th meeting of the Japan Veterinary Society]. Therefore, both TK and gA genes are not practical.

The gA as well as gB are one of major glycoproteins produced by the virus. Although it is known that inoculation of gB induces the production of a neutralizing antibody in animal body, it has not yet been observed by inoculation of gA, nevertheless, it is expected that gA causes a cellular immunization. Therefore, if the Marek's disease virus is desired to have both functions as a vector and as a vaccine, the insertion of an exogenous gene into this gA gene to mutate the gA gene is undesirable since this will deteriorate the function as a vaccine.

Under the circumstances, the present inventors had intensively studied as to less analyzed gene in order to prepare an effective recombinant Marek's disease virus, and as a result, have already found that the recombinant Marek's disease virus could be obtained by using a BamHI—H fragment of the Marek's disease virus type I gene (the 8th fragment from the biggest prepared by digesting the Marek's disease virus gene with the restriction enzyme BamHI) (EP 361182A).

BRIEF SUMMARY OF THE INVENTION

Under such circumstances, the present inventors have further intensively studied to develop a more effective virus vector, and as a result, have found a new site in the Marek's disease virus genome where an exogenous gene can be incorporated quite efficiently and found that the recombinant Marek's disease virus thus obtained was confirmed to show an excellent growth stability in vivo as well as in vitro without losing its intrinsic nature as the Marek's disease virus.

An object of the present invention is to provide a novel recombinant Marek's disease virus useful for an avian vaccine.

A further object of the present invention is to provide a process for preparing said recombinant virus.

Another object of the present invention is to provide a multivalent live vaccine for birds comprising said recombinant Marek's disease virus.

Still another object of the present invention is to provide a vector for administration of a physilogically active substance such as a hormone into the chicken body.

These and the other objects and the advantages of the invention will be apparent to those skilled in the art from the following description.

BRIEF DESCRIPTION OF THE DRAWINGS

FIGS. 12A and 12B show a nucleotide sequence of the A6 fragment of BC-1 strain.

FIG. 14 shows a nucleotide sequence of ORF consisting of Us639 containing the BalI site and the vicinity thereof in the A4 fragment of 61-554 strain.

DETAILED EXPLANATION OF THE INVENTION

Figure 1:
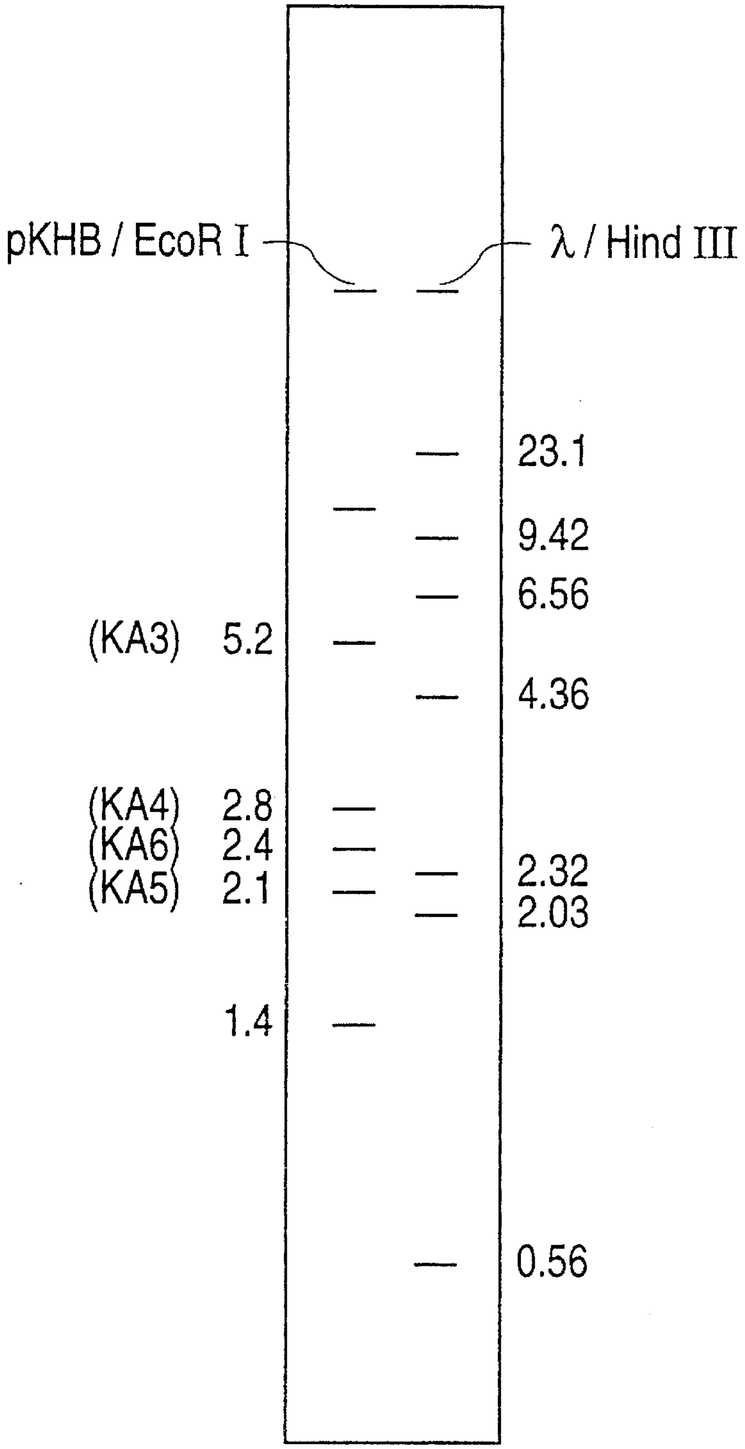
FIG. 1 is an illustration showing a pattern of the EcoRI digestion of pKHB which is a subcloned plasmid of DNA of a Marek's disease virus type I strain: 61-554 strain.

As a vaccine against Marek's disease, there have hitherto been known those comprising an attenuated Marek's disease virus type I (MDV-I), herpes virus of turkey (HVT: MDV-III) or a mixture of Marek's disease virus type II and herpes virus of turkey. Since it has been found that Marek's disease itself is induced by the infection of type I virus, it is preferable to use an attenuated vaccine of the serologically homologous virus, i.e. Marek's disease virus type I, for prevention of outbreak of the disease. In the preferred embodiment of the present invention, accordingly, Marek's disease virus type I is used for preparing the recombinant Marek's disease virus of the present invention which is useful as a multivalent vaccine including Marek's disease vaccine.

The present inventors have found two regions suitable for insertion of an exogenous gene which are useful for preparation of a recombinant Marek's disease virus, i.e. the Us region and inverted repeat sequences of the Marek's disease viral genome. The Us region is referred to a gene sequence of about 12 kb situated at the 3' end of MDV DNA, which is sandwiched between the inverted repeat sequences. By incorporating an exogenous gene into the region, it becomes possible to stably express a desired exogenous gene and to prepare a recombinant Marek's disease virus without loss or decrease of the features of the Marek's disease virus which is necessary for preparing Marek's disease vaccine.

A gene fragment derived from the Us region of the Marek's disease virus used in the present invention is a gene fragment derived from the Us region of at least about 1 kb which contains an insertion site capable of incorporating an exogenous gene, for example, a suitable restriction enzyme site. A preferable gene fragment derived from the Us region includes a gene fragment of about 2.8 kbp containing the BalI site which is produced by treating a gene of Marek's disease virus type I with the restriction enzyme EcoRI (A4 fragment). The spontaneous repeat sequence in the inverted repeat sequence of the present invention can be removed without affecting the viral growth and hence this repeat sequence is also suitable for incorporating an exogenous gene without affecting the viral growth like the above fragment.

It has not yet been reported that an antibody against a produce of a gene inserted into the viral genome is produced and maintained for a long period of time in a chicken inoculated with the recombinant Marek's disease virus. In addition, there has not yet been developed an excellent immunological method like the present invention, i.e. the method wherein an antibody against a protein expressed in cells such as β-galactosidase is produced and maintained for a long period of time as long as more than 4 months by only one inoculation immediately after the birth. Therefore, it is expected that much stronger immunization is induced by expressing in the body of chicken a protein which is expressed on the surface of infected cells such as a membrane protein of Newcastle disease virus (hereinafter referred to as "NDV") or infectious bronchitis virus (hereinafter referred to as "IBV") by using the immunological method of the present invention. In fact, as disclosed in the present invention, the recombinant Marek's disease virus wherein a gene coding for NDV fusion protein (abbreviated as NDV-F protein) is inserted showed an effect to sufficiently prevent the Newcastle disease for more than 4 months after the innoculation. As to a protein which intrinsically is not expressed on or outside of the cell membrane, a gene coding for such a protein can be designed so that the protein can be excreted out of the cells by adding a signal peptide at the N terminus [Nucleic Acids Research, 14, 4683–4690 (1986)] or the protein is expressed on the cell membrane by adding an anchor region rich in hydrophobic amino acids at the C terminus. By the manner of these expressions, much stronger immunization can be induced against the expression products of the inserted gene.

It is known that the virus of which a part of genes is inactivated by the insertion of an exogenous gene usually shows a reduced growth or pathogenicity as a parameter of the growth in vivo even though the virus shows an excellent growth in vitro [Bernard Meignier et al., The Herpes Viruses 4, 265 (1985)]. Therefore, in order to ascertain whether the prepared recombinant virus or vaccines can be used in vivo, it is necessary to confirm whether the virus actually grows and shows immunogenicity when the obtained virus is inoculated into a chicken. From this point of view, the present inventors have conducted an experiment for confirmation of the effect of the prepared recombinant virus wherein the virus is inoculated into chicken. As a result, it was confirmed that the recombinant Marek's disease virus prepared in accordance with the method of the present invention kept on infecting in the body of chicken for more than 16 weeks and hence retained its ability to grow in vivo. In addition, its excellent immunognicity was confirmed by the continuous production of an antibody against the Marek's disease virus, the continuous production of an antibody against the product of the inserted gene, i.e. β-galactosidase, and excellent effects to prevent the Marek's disease and the Newcastle disease.

As mentioned above, the recombinant Marek's disease virus prepared by the method of the present invention well grows and continuously infects in the body of chicken and not only shows an effect to prevent the virulent Marek's disease virus but also is capable of producing an antibody against a product of the exogenous gene. The most characteristic feature of the present invention is the technique to prepare the recombinant virus having the above-mentioned excellent growth and immunogenity in vivo, by which the in vivo application is possible i.e. the recombinant multivalent live vaccine can actually be prepared, which has hitherto never been achieved.

Accordingly, when an exogenous gene coding for a vaccine antigen for other diseases is incorporated into Marek's disease virus and the recombinant virus is inoculated to birds, the antigen derived from the exogenous gene is continuously expressed for a long period of time or all life of the host birds by the same mechanism as Marek's disease virus, and thereby humoral or cell-mediated immunity against said antigen is continuously induced for a long period of time or all life of the host. That is, in accordance with the present invention, a multivalent live vaccine can be prepared which can afford immunity against a number of pathogens only by a single administration to birds such as chick when hatched.

In addition, since the recombinant virus of the present invention can keep on expressing β-galactosidase in the body of chicken for a long period of time, the vector system of the present invention can be used not only as a system for administration of an antigen but also as a drug delivery system for administration of a physiologically active substance such as a hormone into the living body.

The preparation of the recombinant Marek's disease virus of the present invention is described in more detail hereinbelow.

Generally, the preparation of th recombinant virus of the present invention is carried out by the following procedures:

(i) A part of viral DNA is clone in a plasmid vector.

(ii) An insertion plasmid is constructed by inserting a gene fragment enabling an expression of an exogenous gene into a plasmid in which the viral DNA fragment is cloned.

(iii) Said insertion plasmid is transduced into virus-infected cells.

(iv) A recombinant virus containing the exogenous gene is selected by a suitable method.

The insertion plasmid used for incorporating the exogenous gene into the virus basically contains a gene coding for the Us region or the inverted repeat sequence derived from the Marek's disease virus, a promoter derived from an animal cell or an animal virus, a structural gene coding for a desired exogenous protein bound downstream of said promoter, and optionally a transcription terminater bound downstream of said structural gene. The recombinant gene fragment wherein the promoter and the structural gene coding for the exogenous protein and optionally the transcription terminater are designed so that said gene coding for the exogenous protein can be transcribed and translated is designated as "exogenous gene expression cassette". Therefore, the insertion plasmid of the present invention may also be referred to as a plasmid which contains the Us region or the inverted repeat sequence derived from the Marek's disease virus into which the exogenous gene expression cassette is incorporated. By using this insertion plasmid, the virus-derived gene fragment in the plasmid is substituted for the homologous moiety in the viral DNA genome and thereby the exogenous gene fragment is incorporated into the vital genome. The promoter derived from an animal cell or an animal virus used herein includes various known promoters used in a plasmid for expression in an animal cell and is not limited to a specific promoter.

In the above procedure (i), the Viral DNA is firstly digested with a restriction enzyme and then the digested products are subjected to an agarose gel electrophoresis to separate fragments from each other and to collect each fragment from the gel. Each of the obtained fragments is cloned in a plasmid.

In the procedure (ii), each vital fragment cloned in the plasmid in the above procedure (i) is digested with an appropriate restriction enzyme at one site or at two sites to delete a part of the viral fragment and thereto are incorporated a promoter capable of functioning in an animal cell and further a structural gene coding for a desired exogenous protein downstream of said promoter.

The procedure (iii) is effected for a homologous recombination of a viral DNA fragment including an exogenous gene into a viral DNA and is usually conducted by simultaneously transducing cells with the infectious viral DNA and the insertion plasmid. In the present invention, however, it is effected by firstly infecting the culture cells with the virus and then introducing the above insertion plasmid into said infected cells. Accordingly, the method of the present invention is a quite simple method for recombination to obtain the recombinant virus at a quite high level of efficiency by using an electroporation method for the transduction.

The exogenous gene to be incorporated into the Marek's disease virus genome includes various genes coding for a protein which is capable of acting as a vaccine antigen for a variety of chicken diseases such as a varial disease, a bacterial disease, a parasitic disease, etc. In case of a multivalent vaccine for chicken, the exogenous gene to be incorporated includes, for example, a gene coding for an antigen of the Newcastle disease virus (NDV), e.g. a gene coding for NDV-F protein or hemagglutinin neuraminidase protein (abbreviated as HN protein), a gene coding for a glycoprotein of the chicken infectious laryngotracheitis virus (ILTV), a gene coding for a viral structural protein of the infectious bursa of Fabricius disease virus (IBDV), e.g. a gene coding for VP2, a gene coding for a spike protein of the infectious bronchitis virus (IBV) and a gene coding for HA protein of *Heamophilus paragallinarum* which causes an infectious coryza, and the like.

In one embodiment of the recombinant live vaccine of the present invention, a recombinant Marek's disease virus for preventing the Newcastle disease and a process for the construction thereof as well as effects thereof are described herein. As a gene of the Newcastle disease virus to be incorporated into the recombinant virus, a cDNA derived from an extremely attenuated strain D-26 is used. The pathogenicity of the Newcastle disease virus is determined by whether the fusion protein (abbreviated as F protein) is virulent or not or whether the HN protein is virulent or not. When the recombinant virus is prepared by using the virulent F gene or HN gene, there is a possibility that the vector virus may obtain the pathogenicity from the virulent gene. In order to avoid this dangerous possibility, the recombinant virus of the present invention is prepared by using genes derived from the extremely attenuated strain D-26.

That is, the present invention can provide a quite excellent live vaccine having such a long lasting effect that can not be shown by the conventional vaccine for the Newcastle disease, and further having high safety.

The recombinant Marek's disease viral vector of the present invention is also useful as a vector for administration of a chicken growth hormone or an immunizator as well as an antigen for prevention of infection. The recombinant vector of the present invention can also be used for administration of an antigen for immunization of a chicken for breeding, in order to impart the ovum the ability to produce a variety of useful antibodies. That is, the recombinant Marek's disease virus of the present invention can be used for incorporation of these genes into a vector which is useful in a drug delivery system (hereinafter referred to as "DDS").

The selection of the recombinant virus containing the desired exogenous gene in the procedure (iv) can be carried out by the most suitable means depending on a kind of the exogenous gene to be incorporated into the vital DNA. For example, when the recombinant Marek's disease virus capable of expressing the Newcastle disease virus F antigen is prepared in order to obtain a multivalent vaccine useful for Newcastle disease as well as Marek's disease, the desired recombinant Marek's disease virus which can also be used as a vaccine for Newcastle disease can be selected by detecting the NDV-F antigen. On the other hand, when a gene coding for an enzyme is incorporated into the recombinant Marek's disease virus, the desired virus can be screened based on the activity of the enzyme. For example, in case of the selection of a recombinant virus herein a gene coding for β-galactosidase (β-gal) (which is hereinafter referred to as "LacZ gene") is incorporated into the Marek's disease virus for expressing β-galactosidase, a substrate of β-galactosidase [e.g. X-Gal (5-bromo-4-chloro-3-indolyl-β-D-galactopyranoside)] is added to an agar-overlayed cell sheet, by which a plaque of virus showing the β-galactosidase activity can be distinguished by color [S. CHAKRABBARTI et al., Mol. Cell. Biol., 5, 3403 (1985); Saeki et al., Abstract of the 35th Meeting of Japan Virology Society (1987)].

Moreover, a recombinant MDV in which an objective foreign gene is inserted is easily prepared by using the cell free type-LacZ(+) virus (β-gal(−) virus) described above as a parent cell and cloning a LacZ(−) virus from supernatant of recombinant plaques in which the LacZ gene is replaced with the objective foreign gene (hereinafter referred to as "reverse method"). This reverse method is a very convenient method for constructing a recombinant virus inserted with the objective foreign gene. Since conventional MDV1 yielded very few cell-free virus, it was impossible to adapt the reverse method to conventional MDV1 or cell-associated virus. Namely, in case of cell-associated virus, it is necessary to screen from the various recombinant plaques which include appropriately recombined LacZ(−) virus and inappropriately unrecombined LacZ(+) virus. However, it is difficult to screen the appropriately recombined LacZ(−) virus. On the other hand, the objective recombined virus (reversed virus) is easily prepared by using the cell free type-MDV of the present invention.

The present invention is more specifically illustrated by the following Examples but should not be construed to be limited thereto.

Viral strain 61-554 Strain of Marek's disease virus type I isolated from the field was used. This strain has been isolated from a broiler of 50 days old which has not been inoculated with the Marek's disease vaccine in 1986. When this strain was tested by inoculation of $2\times10^3$ PFU of the strain into the peritoneal of SPF (specified-pathogene-free) chick of 1 day old, the onset of the disease or the death of the animal was not observed during 10 weeks test period and also the autopsy could not reveal any disorder such as tumor.

Purification of viral DNA

After inoculating the virus into chick embryo fibroblasts (hereinafter referred to as "CEF"), the virus-infected cells were harvested at the time when cytopathic effect (CPE) was strongly shown and the viral DNA was purified according to the method of Hirai et al., [J. Gen. Virol., 45, 119 (1979)].

That is, the virus-infected cells which showed strong CPE were collected by centrifugation and thereto was added a double amount of a 1% NP40 solution (0.01M Tris-HCl, pH 7.4, 0.01M Nacl, 0.0015M $MgCl_2$) and the mixture was ice-cooled for 30 minutes and then pipetted. After the solution was centrifuged at 2,500 rpm for 10 minutes, the supernatant was overlayed on a 40%–60% (w/w) sucrose solution (0.02M Tris-HCl, pH 7.4, 0.15M NaCl). After centrifugation at 175 KG for 2 hours, a layer containing a capsid derived from the Marek's disease virus, the layer being formed between the 40% sucrose solution and the 60% sucrose solution, was separated. This intermediate layer was resuspended in a solution containing 0.02M Tris-HCl, pH 7.4 and 0.15M NaCl and the suspension was centrifuged at 160 KG for 1 hour and pelleted. The obtained pellet was suspended in a 1% SDS solution (0.1% Tris-HCl, pH 7.4, 0.01M EDTA, 1% Sarcosinate; manufactured by Nakarai Kagaku Co. Ltd.,) supplemented with 0.1% Proteinase K (manufactured by Boehringer Mannheim yamanouchi) and the suspension was left to stand at 37° C. overnight. Then DNA was collected by a phenol treatment and an ethanol precipitation. The obtained DNA was dissolved in a TE buffer (10 mM Tris-HCl pH 8.0, 1 mM EDTA) and the solution was overlayed on a 10%–30% glycerol gradient solution, followed by centrifugation at 175 KG for 4 hours. Then the solution was fractionated from the bottom of the centrifuge tube and a fraction containing the viral DNA was separated. An equivalent amount of a 10% trichloroaetic acid was added to the viral DNA-containing fraction to precipitate DNA and the precipitated DNA was collected.

Cloning of viral DNA

Then, the above purified Marek's disease viral DNA (1 μg) was digested with a restriction enzyme and the obtained fragments were subjected to a 0.9% agarose gel electrophoresis to separate from each other and the separated fragments were eluted from the gel by an electro-elution procedure, followed by collection by a phenol treatment and an ethanol precipitation. The thus obtained fragment was ligated to pUC or PBR plasmid with T4 DNA ligase. Suitable competent cells (e.g. JM109) were transduced with the ligate to give transformed E. coli cells. The transduced cells were then cultured on an LB medium supplemented with ampicillin (100 μg/ml). Plasmids within cells were collected by the conventional alkali procedure.

Determination of nucleotide sequence

The obtained gene fragment was inserted into the polylinker of pUC119 and tranduced into competent cells such as JM109. The obtained transformants were cultured on an LB medium overnight and then 30 μl of the culture was infected with M13 phage (more than $10^9$/ml; 60 μl) and the culture was further continued overnight. The cells were removed by a centrifugation and the phage was collected from the supernatant. Then, a single strain DNA (hereinafter referred to as "ss DNA") containing a nucleotide sequence of a desired gene fragment was prepared by the usual method.

Using SEQUENASE V2.0 (manufactured by TOYOBO), the nucleotide sequence of the obtained ss DNA was determined according to the protocol.

If necessary, the gene fragment on the plasmid was stepwise shortened by using the Deletion Kit for Kilo-Sequence (manufactured by Takara; cat. No. 6030), plasmids were reconstructed using the obtained shortened gene fragments and the ss DNAs were prepared in the same manner.

Preparation of recombinant virus

Primary CEF cultured at 37° C. overnight were harvested with an EDTA-trypsin solution and then suspended in an Eagle-MEM (E-MEM; manufactured by Nissui Co. Ltd.,) medium supplemented with a 5% bovine serum (hereinafter referred to as "BS") at a cell concentration of $2\times10^5$ cells/ml. Forty milliliters of the suspension was put in a tissue culture flask manufactured by Falcon (No. 3028). Thereto were inoculated CEF infected with the Marek's disease virus at about $8\times10^5$ cells and the cells were cultured at 37° C. for 4 hours. Thereafter, the cells were again harvested with the EDTA-trypsin solution and washed twice with a phosphate-buffered saline (abbreviated as PBS(−)). The cells ($5\times10^5$ cells) were transferred to the cuvette of Gene Pulser (manufactured by Bio-Rad; cat. No. 165-2075). To the cuvette was added the insertion plasmid and thereto was added the pulse in accordance with the protocol to induce the insertion plasmid into the virus-infected cells. The cells were then suspended in E-MEM (manufactured by Nissui Co. Ltd.; 15 ml) supplemented with 5% BS, transfered to Petri dish of 10 cm diameter (manufactured by Falcon; cat. No. 3003) and cultured at 37° C. Next day, dead cells which did not took to the dish were removed together with the culture medium and to the dish was added E-MEM (15 ml) supplemented with 5% BS in which primary CEF cultured on the previous day (2nd CEF) were additionally suspended at $5\times10^5$ cells/ml. After culturing the cells at 37° C. for 4 or 7 days, on the cultured cells was overlayed 1% agarose/E-MEM solution (containing no phenol red) supplemented with chlorophenol red β-D-galactopyranoside (manufactured by Seikagaku Kogyo; 100 μg/ml).

Red plaques showing the β-gal activity appeared within 5 to 60 minutes and were subcultured by a plaque cloning. This procedure was repeated several times and then virus-infected cells were moderately disintegrated with an ultrasonic disintegrator to give cell-free viruses. The obtained cell-free viruses were inoculated to CEF, which have been cultured for 4 hours, and cultured for several days. The plaque cloning was further conducted twice or thrice to purify the recombinant virus.

Southern hybridization

Using DIG-DNA Labelling Kit (manufactured by Boehringer Mannheim yamanouchi; cat. No. 150350) and Southern-light (manufactured by TROPIX; cat. No. SL100), the probes were prepared and the hybridization was conducted according to the protocols. Briefly, the DNA was linearized and denatured by heating and the probe DNA was synthesized using a random primer, Klenow fragment and dNTPs including digoxigenin-labelled dUTP as a substrate.

The obtained probe was hybridized with the desired DNA transfered to Hybond N+ (manufactured by Amersham Japan; cat. No. RPN.303B) in accordance with the protocol and detected with an alkaliphosphatase-labelled anti-digoxigenin sheep IgG. 3-(2'-Spiroadamantane)-4-methoxy-4-(3"-phosphoryloxy)-phenyl-1,2-dioxetane (AMPPD) was used as a substrate of the enzyme alkaliphosphatase and the obtained specific luminescence was detected with X-ray film (manufactured by FUJIXEROX; X-OMAT).

Collection of recombinant viral DNA

A supernatant was removed by suction when the viruses inoculated on the Petri dish (manufactured by Falcon; cat. No. 150350) showed CPE all over the dish. A solution (2 ml) of Proteinase K (Proteinaise K 1 mg/ml, 0.1M-Tris HCl, pH 9.0, 0.1M-NaCl, 0.001M-EDTA, 1% SDS) was poured onto the dish and the cells were treated at 37° C. for 1 hour. The cells were then transfered to conical tube (manufactured by Falcon; cat. No. 2099) and treated at 37° C. overnight. Then, the cells were treated with phenol and the supernatant was subjected to ethanol precipitation. After drying, the precipitate was dissolved in 100 μl of TE (10 mM-Tris HCl pH 8.0, 1 mM-EDTA). For Southern hybridization, 2 μl of this solution was used after digestion with a restriction enzyme.

Collection of viruses from chicken body

Blood (1 ml) was taken with a syringe containing heparin. To this blood was added PBS(−) so that the total volume becomes 4 ml and the mixture was quietly overlayed on Ficoll-Pque (manufactured by Falmacia; 3 ml) contained in conical tube (manufactured by Falcon; ca. No. 2099), which was subjected to centrifugation at 1500 rpm for 30 minutes (KN-30F, manufactured by KUBOTA).

The intermediate layer containing lymphocytes and monocytes (Buffy coat) was separated and again suspended in PBS(−) containing 0.01% EDTA. The suspension was subjected to centrifugation at 1000 rpm for 5 minutes to recover the lymphocytes and monocytes, which were inoculated to the secondary CEF cultured for 4 hours. CEF were observed for 4 to 7 days. CEF which showed no CPE by MDV were subcultured to the third generation and then the presence of CPE was determined.

Fluorescent antibody (FA) method

The 61-554 strain ($10^4$ PFU) was inoculated on the Petri dish (diameter: 5 cm) containing three cover glasses (manufactured by MATUNAMI, No. 1, 18×18 mm) together with CEF ($10^7$ cells) and cultured for 2 days. The cover glasses were taken out, acetone-fixed at room temperature for 20 minutes and stored at −80° C. For detection of an anti-β-gal antibody, BMT-10 cells were incorporated with the plasmid pASLacZ wherein the LacZ gene is bound downstream of the β-actin promoter [Japanse Patent Application No. 226960/1988 (Japanese Patent First Publication No. 76578/1990)] by electroporation and then cultured for 2 days. The cells were acetone-fixed in the same manner as mentioned above and stored at −80° C.

Chicken serum was diluted (×10) with PBS(−) and allowed to stand at 4° C. overnight. Thereto was added FITC-labelled anti-chicken IgG goat antibody (manufactured by KIRKEGAARD & PERRY Lab., cat. No. 031506) diluted by 20-fold with PBS(−). After reaction at 37° C. for 1 hour and washing, the observation was conducted under a fluescent microscope.

ELISA

β-Gal (manufactured by TOYOBO, c©de No. GAH-201; 20 ml) was poured into a 96-well flatbottomed plate (manufactured by Nunc, cat. No. 473768) at 100 μl per well and reacted at 4° C. overnight. After washing with 0.15M-PBS(−) (pH 7.3), the plate was blocked with 1% BSA/0.15M-PBS(−) at 37° C. for 2 hours.

After diluting the test sera by 800-fold with PBS(−), 100 μl of the diluted test sera was added to the plate and reacted at 37° C. for 1 hour. Thereafter, according to a known method, an anti-chicken IgG POD-labelled rabbit antibody (Nordick) and TMBZ (manufactured by Dojin Kagaku; cat. No. 346-04031) were reacted with the plate. After the reaction was quenched with 1N $H_2SO_4$, the absorption at OD450 nm/630 nm was measured and the value obtained by subtracting the absorption at 630 nm from the absorption at 450 nm was regarded as ELISA value.

EXAMPLE 1

(Cloning of DNA of Marek's disease virus type I 61-554 strain)

DNA (1 μg) of the 61-554 strain was digested with HindIII and the obtained fragments were subjected to 0.7% agarose gel electrophoresis. The fragment of 17 kb (hereinafter referred to as "HindIII—B fragment") was taken out from the gel and cloned in pBR322. This HindIII—B fragment was digested with EcoRI and subcloned in a plasmid pUC119 wherein the region of from the BamHI site to the HindIII site in the multicloning site (MCS) was removed (hereinafter referred to as "Δpuc119"), said subcloned plasmid being referred to as "pKHB". FIG. 1 shows a pattern of the EcoRI digestion of pKHB.

Figure 2:
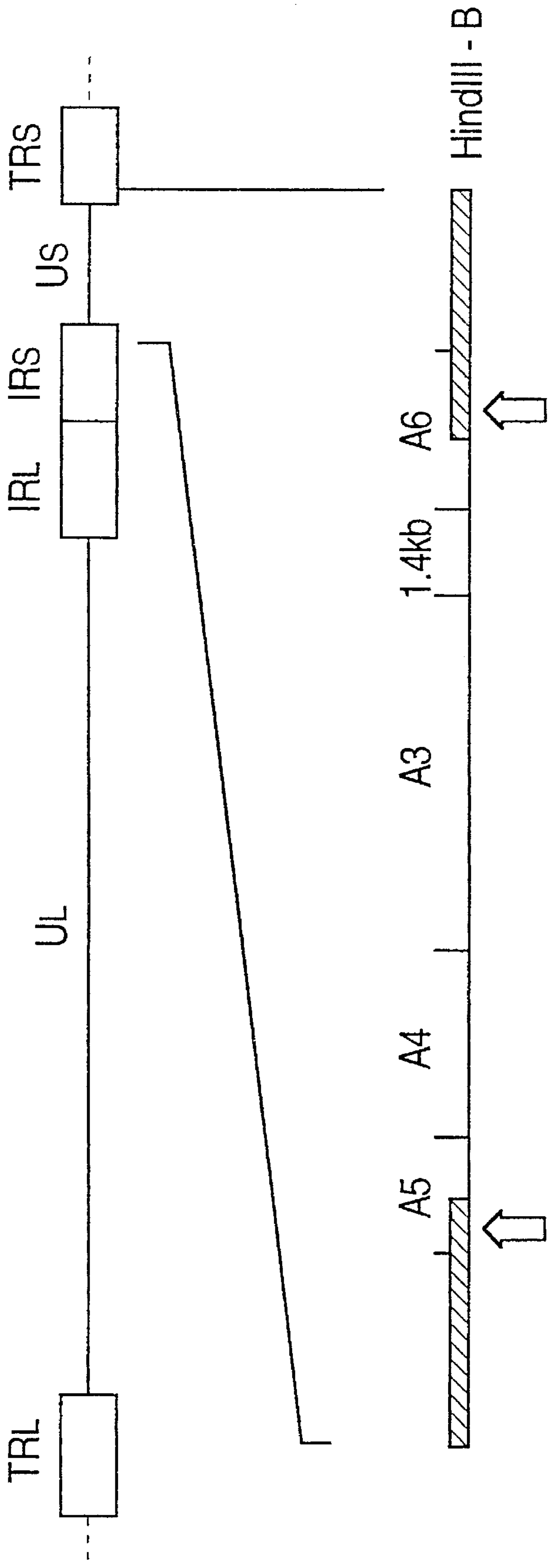
FIG. 2 shows a position of A4, A5 and A6 fragments of the 61-554 strain on the genome.

The position of the EcoRI subfragment, A3 (5.2 kb), A4 (2.8 kb), A5 (2.1 kb) and A6 (2.4 kb), is shown in FIG. 2. Plasmids containing each of these fragments were named as pKA3, pKA4, pKA5 and pKA6, respectively. Among these fragments, A5 and A6 fragments were shown to have a different size depending on a kind of virus strains (cf. Table 1).

TABLE 1

| | Strain | | | |
|---|---|---|---|---|
| EcoRI fragment | GA | 61-554 | CVI988 | BC-1 |
| A3 | 5.2 kb | 5.2 kb | 5.2 kb | nt |
| A4 | 2.8 kb | 2.8 kb | 2.8 kb | nt |
| A5 | 1.8 kb | 2.1 kb | 1.9 kb | nt |
| A6 | nt | 2.4 kb | 2.5 kb | 3.1 kb |

(Note) nt: not tested

EXAMPLE 2

Figure 3:
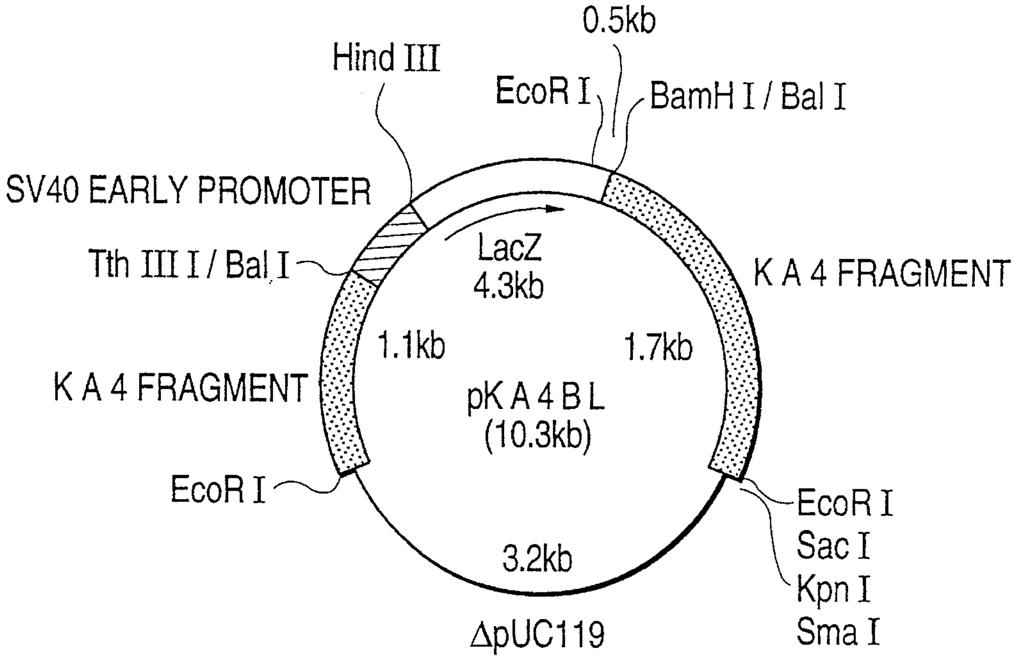
FIG. 3 shows the insertion plasmid pKA4BL used for preparation of a recombinant Marek's disease virus K-A4BL.

(Preparation of a recombinant Marek's disease virus inserted with SV40-LacZ gene; K-A4BL)

pCH110 (manufactured by Pharamacia, cat. No. 27-4508-01) was digested with BamHI and TthIII I and the obtained fragment of 4.2 kb was blunt-ended (SV40-LacZ), which was incorporated into the BalI site of pKA4 (insertion plasmid pKA4BL) (cf. FIG. 3).

After pKA4BL was linearized by digestion with KpnI, the recombinant virus K-A4BL was prepared by the method described in Preparation of recombinant virus. This recombinant virus showed an excellent growth in vitro equivalent to the parent viral strain 61-554.

Figure 4:
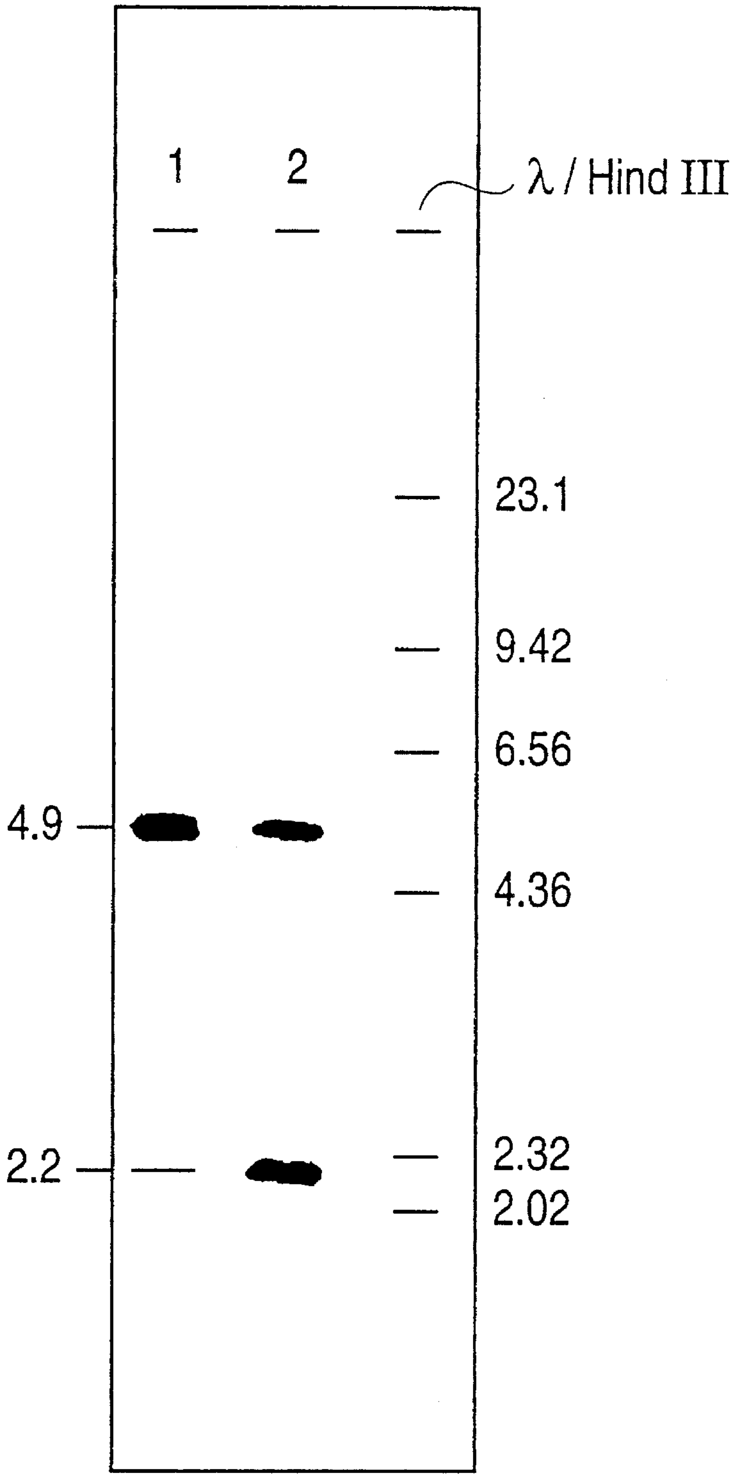
FIG. 4 is an illustration showing results of Southern hybridization which was conducted on the digestion product of DNAs extracted from CEF infected with K-A4BL with the restriction enzyme EcoRI using LacZ gene (lane 1) and KA4 fragment (lane 2) as a probe.

In order to confirm the position where the LacZ gene is incorporated in K-A4BL, DNAs extracted from CEF infected with K-A4BL were digested with EoRI and the obtained fragments were subjected to Southern hybridization. FIG. 4 shows results of Southern hybridization in which the KA4 fragment and the LacZ gene (3.7 kb) taken out of pCH110 by digestion with HindIII and BamHI were used as probes. In both cases using the KA4 fragment (lane 2) and the LacZ gene (lane 1) as the probe, only bands having the expected size were detected and thereby it was confirmed that the incorporation of the LacZ gene was made by the homologous recombination and the recombinant virus was purified.

Figure 5:
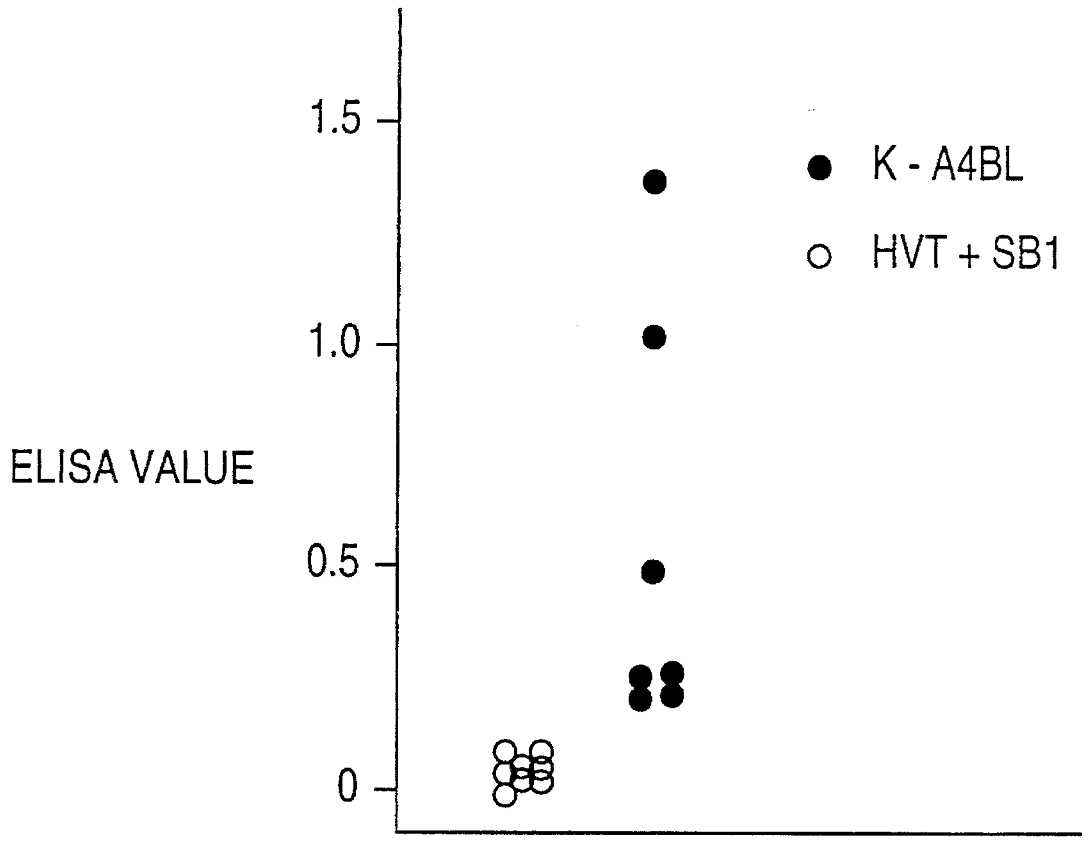
FIG. 5 is a graph showing a serum level of anti-β gal ELISA antibody in chicken of 7 weeks old which has been inoculated with K-A4BL 7000 PFU at one day old wherein the white circle shows the serum level in chicken of 7 weeks old which has been inoculated with the conventional divalent vaccine of Marek's disease virus.

Table 2 shows results of the virus recovery test and the anti-MDV fluorescent antibody (hereinafter referred to as "FA") test in SPF chicks of 1 day old inoculated with K-A4BL (7000 PFU). The virus recovery of 1 week and 6 weeks after the inoculation was 4/5 and 5/5(+), respectively, and the anti-MDV FA of 6 weeks after the inoculation was 7/7(+). On the other hand, the anti-β-gal antibody titer was measured by ELISA for sera of 7 weeks after the inoculation. As shown in FIG. 5, all of the seven cases showed higher values than those of controls (inoculated with HVT+SB-1) and were positive even in FA against the antigen β-gal, the detection of which was less sensitive, and thereby the production of the anti-β-gal antibody in the chick inoculated with K-A4BL was confirmed. In addition, all the cases were positive for the anti-β-gal antibody even 16 weeks after the inoculation and the virus recovery of 16 weeks after the inoculation also showed good results as 2/7(+). At this stage, the virus recovery from chicks inoculated with 20,000 PFU of HVT or CVI988 clone C was 2/12(+) [Witter et al., Avian Diseases 31, 829–840 (1987)]. That is, according to the results of the tests in this Example, A4BL was confirmed to have a persistent infectivity which is equivalent to or superior to the parent Marek's disease vaccine virus strain and hence to be quite suitable for use as a vector.

Surprisingly, the anti-β-gal antibody was detected in all chickens four weeks after inoculation and the FA value 160 or more were continued more than four months. These results demonstrate that this system is a very excellent way to administer a vaccine to chickens.

In addition, all plaques of the recombinant virus recovered from peripheral blood of 6 weeks after the inoculation showed β-galactosidase activity and hence it was confirmed that the vector of the present invention is useful not only as a system for transiently administering an antigen but also as DDS for continuously producing a physiologically active substance such as an enzyme or a hormone within the living body.

TABLE 2

| Inoculated Virus | Amount (PFU) | Test item | Weeks after inoculation 1 | 4 | 6 | 16 |
|---|---|---|---|---|---|---|
| K-A4BL | 7000 | Virus recovery | 4/5[1] | NT[2] | 5/5 | 2/7 |
| | | FA (anti-MDV) | NT | 4/5 | 7/7 | 7/7 |
| | | FA (anti-βgal) | NT | 5/5 | 7/7 | 7/7 |
| Not ino- | — | Virus recovery | NT | NT | 0/7 | 0/5 |
| culated | | FA (anti-MDV) | NT | NT | 0/7 | 0/5 |
| (Contacted) | | FA (anti-βgal) | NT | NT | 0/7 | 0/5 |

(Note) [1)]Positive No./Test No.;
[2)]Not tested

On the other hand, in case of the chicks which were not inoculated with the viruses but breeded in the same isolater as the chicks inoculated with the recombinant virus, both the virus recovery and the antibody titer were negative, showing that the recombinant virus of the present invention does not infect to individuals living in the same place. That is, the recombinant virus of the present invention is quite practical from the viewpoint that it remains within the individuals inoculated therewith.

In order to confirm the effects of K-A4BL as the vaccine for the Marek's disease, chicks of 1 day old was peritoneally inoculated with 2000 PFU or 6000 PFU of K-A4BL and, a week later, attacked peritoneally with 5000 PFU of virulent Marek's disease virus alabama strain. The chicks were breeded and observed for 10 weeks for the death or the onset of leg palsy due to Marek's disease and the effect of K-A4BL was determined based on the absence of tumor by autopsy after 10 weeks. As the results, as shown in Table 3, the death or the onset of the disease was observed in all of the tested chicks of non-immunized control group but, in case of the group inoculated with K-A4BL, the onset of the disease was observed in only one chick inoculated with 2000 PFU. Therefore, the recombinant virus of the present invention has a sufficient immunogenicity as the vaccine for Marek's disease.

TABLE 3

| Group | Amount (PFU) | Death or onset of disease |
|---|---|---|
| K-A4BL | 2000 | 1/10 |
| K-A4BL | 6000 | 0/10 |
| Control | — | 10/10 |

EXAMPLE 3

Figure 6:
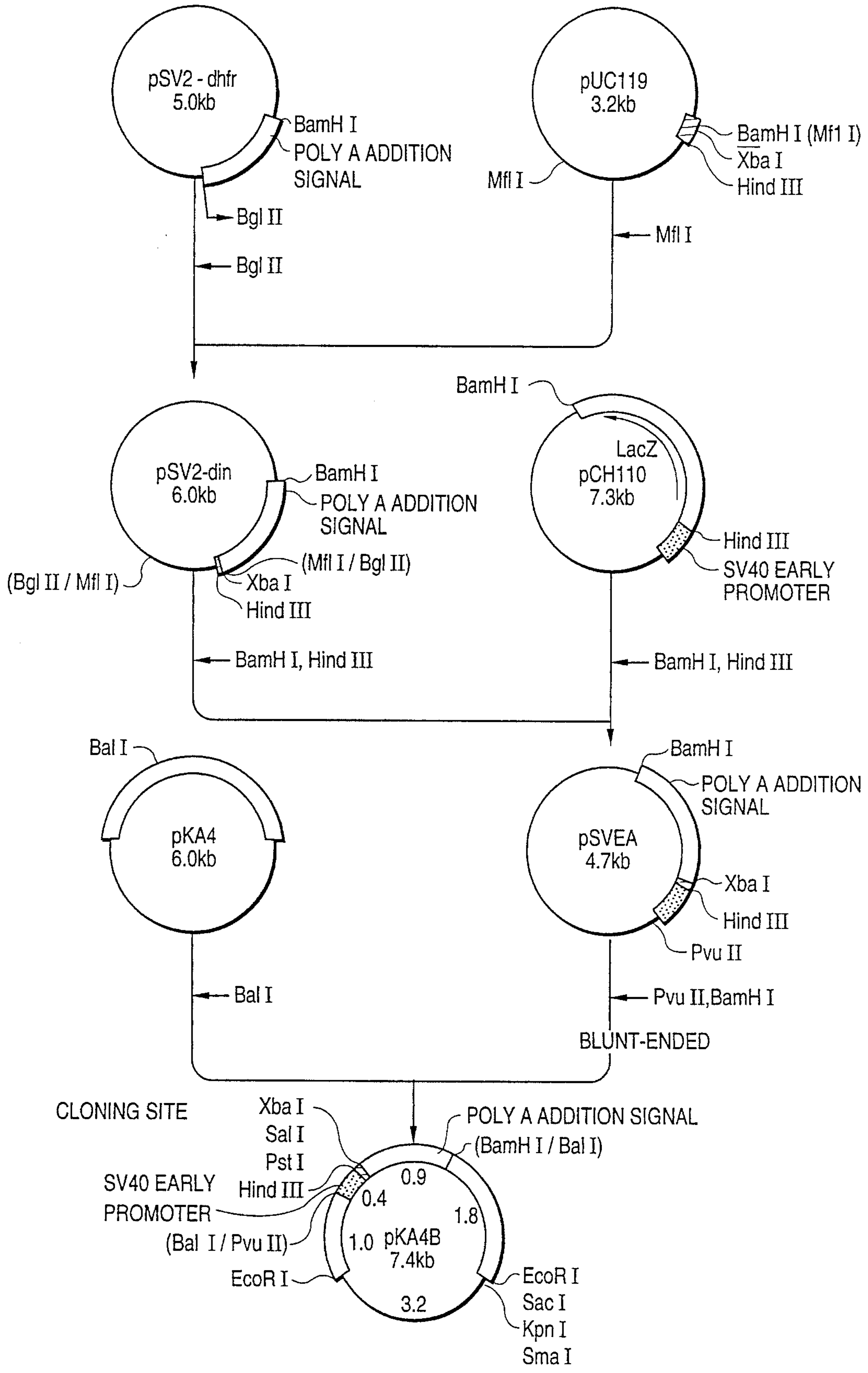
FIG. 6 shows a construction of the insertion vector pKA4B of the present invention.

(Construction of insertion vector pKA4B for preparing recombinant virus)

pUC119 was digested with MflI and the obtained fragments were subjected to 1% agarose gel electrophoresis. A fragment of 1.0 kb containing the region of the multicloning site of from the Hind III site to the XbaI site (hereinafter referred to as "cloning site") was taken out of the gel and inserted into the BglII site of pSV2-dhfr (ATCC No. 371464) (pSV2-dln). This plasmid was digested with HindIII and BamHI and a fragment of 1.0 kb containing the cloning site upstream of the poly A addition signal was obtained and inserted downstream of the SV40 early gene promoter of pCH110 by replacement with the LacZ gene (pSVEA). pSVEA was digested with PvuII and BamHI. A fragment of 1.3 kb containing the SV40 early gene promoter cloning site and the poly A addition signal was blunt-ended and inserted into the BalI site of pKA4 to construct pKA4B (FIG. 6).

Marek's disease virus containing a gene to be expressed can easily be prepared by inserting said gene into the cloning site of pKA4B of the present invention, preparing the recombinant virus and conducting the homologous recombination in accordance with the procedure of Example 2. The protein coded by this gene can efficiently be expressed through the SV40 early gene promoter and the poly A addition signal by introducing said recombinant virus into culture cells or chicks.

EXAMPLE 4

(Preparation of a recombinant Marek's disease virus inserted with a fusion protein gene derived from Newcastle disease virus; K-A4BF)

Figure 7:
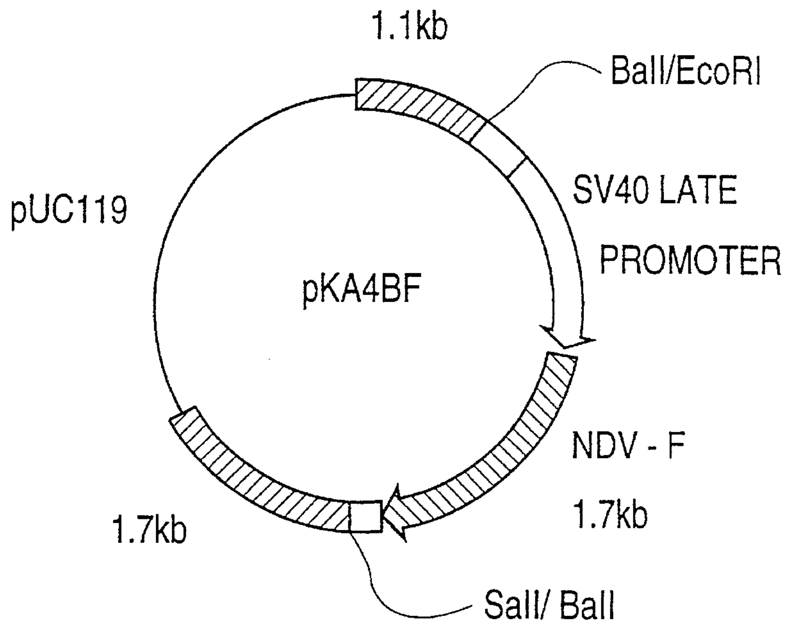
FIG. 7 shows a construction of the insertion vector pKA4BF of the present invention.

A gene coding for a fusion protein (hereinafter referred to as "F gene"; H. Sato et al., Virus Research 7, 241–255 (1987)) derived from the extremely attenuated Newcastle disease virus D-26 strain was incorporated into the SmaI site of pSVL (manufactured by Pharmacia, Code No. 27-4509-01) (pSVLF; FIG. 7). The obtained plasmid was digested with EcoRI and SalI and a fragment of 4.3 kb was collected by the electroelution method. The obtained fragment was blunt-ended and incorporated into the BalI site of pKA4 to construct an insertion plasmid pKA4BF (FIG. 7).

After linearizing the plasmid with PvuI, the recombination was conducted in accordance with the procedure described in Preparation of recombinant virus. The cloning of the recombinant virus was carried out by the immune staining using monoclonal antibodies #83 and #313 recognizing the F protein [Y. Umino et al., J. Gen. Virol., 71, 1199 (1990)].

The cloning of the recombinant virus by the immune staining is described hereinbelow.

Several days after the recombination, the Petri dish with plaques was washed with E-MEM ad thereto an isotonic solution containing the monoclonal antibodies #83 and #313 was added and the mixture was reacted for 10 to 60 minutes, After washing, a peroxidase-labelled anti-mouse antibody (manufactured by Bio-Rad, code No. 172-1011) diluted to 100- to 200-fold with the isotonic solution was added to the dish and the mixture was further reacted at room temperature for 10 to 60 minutes. After washing, to the dish was added 0.1M Tris buffer (pH 7.5) containing 5 mg of 3,3-diaminobenzene tetrahydrochloride (DAB; manufactured by Wako Jun-yaku Kogyo, code No. 343-00901) and 1.6 μl of hydrogen peroxide (manufactured by Mitsubishi Gasu Kagaku, containing 31% $H_2O_2$) per 10 ml and the mixture was further reacted at room temperature for 5 to 60 minutes. The plaque of the recombinant virus changed its color. The plaque stained to brown was surrounded with a ring material. A trypsin solution containing 0.1% EDTA as added only within the ring to recover cells infected with the recombinant virus, which was cultured similtaneously with additional CEF to purify the recombinant virus. The recombinant virus was further purified by, repeating the above procedure and a procedure for preparing cell-free virus by the ultrasonication for several times.

The purified recombinant virus showed an excellent growth in vitro equivallent to the parent strain.

In order to confirm the preventive effects against Newcastle disease (ND) of K-A4BF, an immune test was conducted.

Chicks of 1 day old were peritoneally inoculated with K-A4BF $10^3$ PFU, and 3 weeks, 9 weeksand 16 weeks after the inoculation, attacked intramuscularly at the crus with virulent NDV Sato strain $10^4$ MLD. As the results, by the observation for 2 weeks, the death or the onset of the disease was observed in all of the tested chicks of non-immunized control group but, in case of the group inoculated with K-A4BF, neither of the death or the onset of the disease was observed. Therefore, it was confirmed that the recombinant virus of the present invention has a sufficient effect as the vaccine for Newcastle disease (Table 4).

TABLE 4

(Death or onset of disease)

| Inoculated virus | Amount (PFU) | Weeks after infection 3 | 9 | 16 |
|---|---|---|---|---|
| K-A4BF | 1000 | 0/6 (0/6) | 0/6 (0/6) | 0/6 (0/6) |
| Non-immunized control | — | 6/6 (6/6) | 6/6 (6/6) | 6/6 (5/6) |

EXAMPLE 5

(Preparation of a recombinant Marek's disease virus inserted with HN protein gene derived from a Newcastle disease virus; K-A4BHN)

Figure 8:
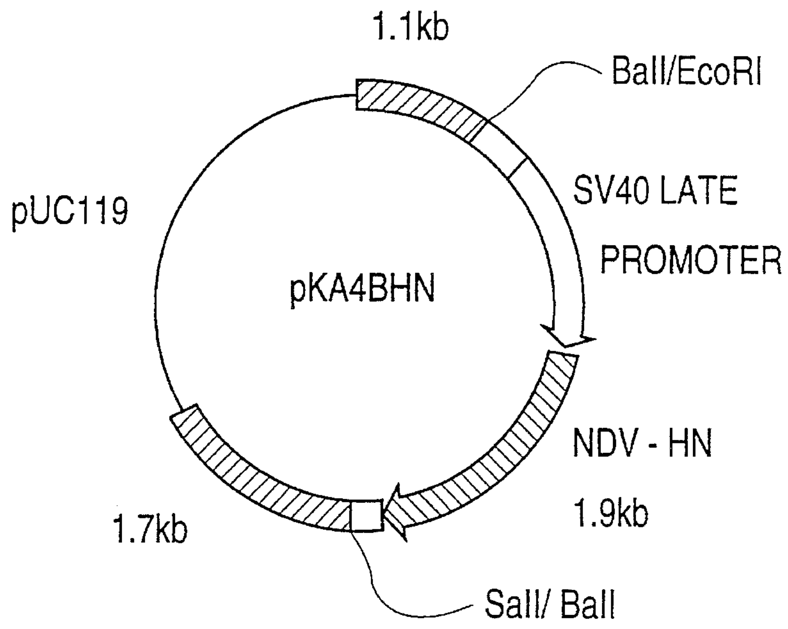
FIG. 8 shows a construction of the insertion vector pKA4BHN of the present invention.

A gene coding for the HN protein derived from the D-26 strain (H. Sato et al., Virus Research 8, 217–232 (1987) was incorporated into the SmaI site of pSVL. The obtained plasmid was digested with EcoRI and SalI and a fragment of 4.5 kb was collected by the electroelution method. The obtained fragment was blunt-ended and inserted into the BalI site of pKA4 to construct an insertion plasmid pKA4BHN (FIG. 8).

After linearizing the plasmid with PvuI, the recombination was conducted in accordance with the procedure for preparing the recombinant virus. The cloning of the recombinant virus was carried out by the immune staining using monoclonal antibodies #193, #142 and #265 recognizing the HN protein [Y. Umino et al., J. Gen. Virol., 71, 1189 (1990)] in the same manner as in the preparation of K-A4BF.

The purified recombinant virus showed an excellent growth in vitro equivallent to the parent strain.

EXAMPLE 6

(Preparation of a recombinant Marek's disease virus inserted with SV40-LacZ gene; K-A3VL)

Figure 9:
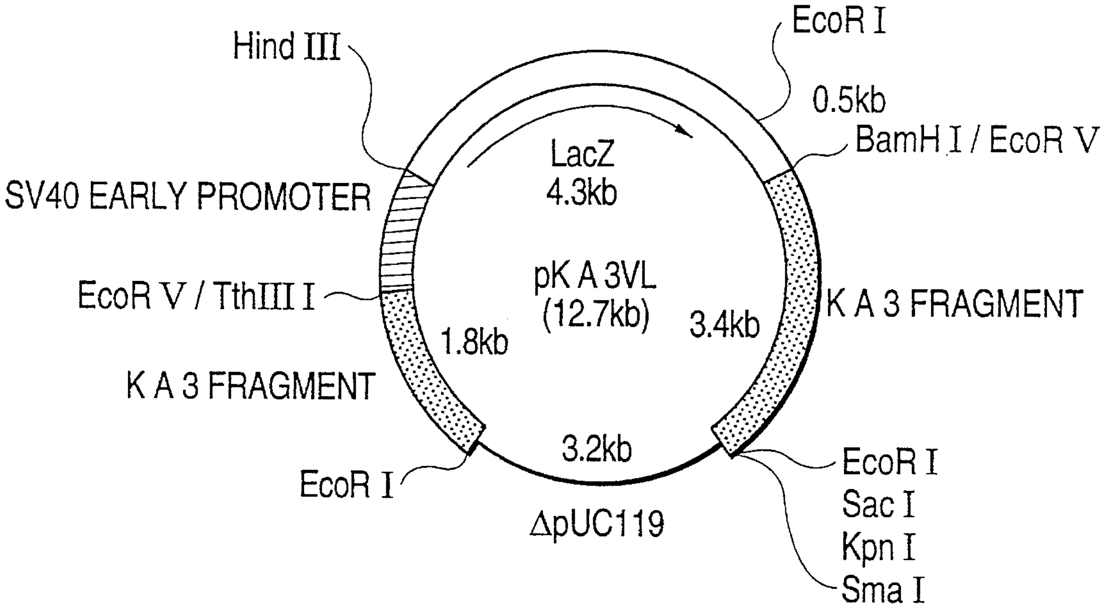
FIG. 9 shows the insertion plasmid pKA3VL used for preparation of another recombinant Marek's disease virus K-A3VL.

SV40-LacZ was incorporated into the EcoRV site of pKA3 (FIG. 9). The obtained plasmid was linearized by digestion and then K-A3VL was prepared in accordance with the procedure for preparing the recombinant virus.

Figure 10:
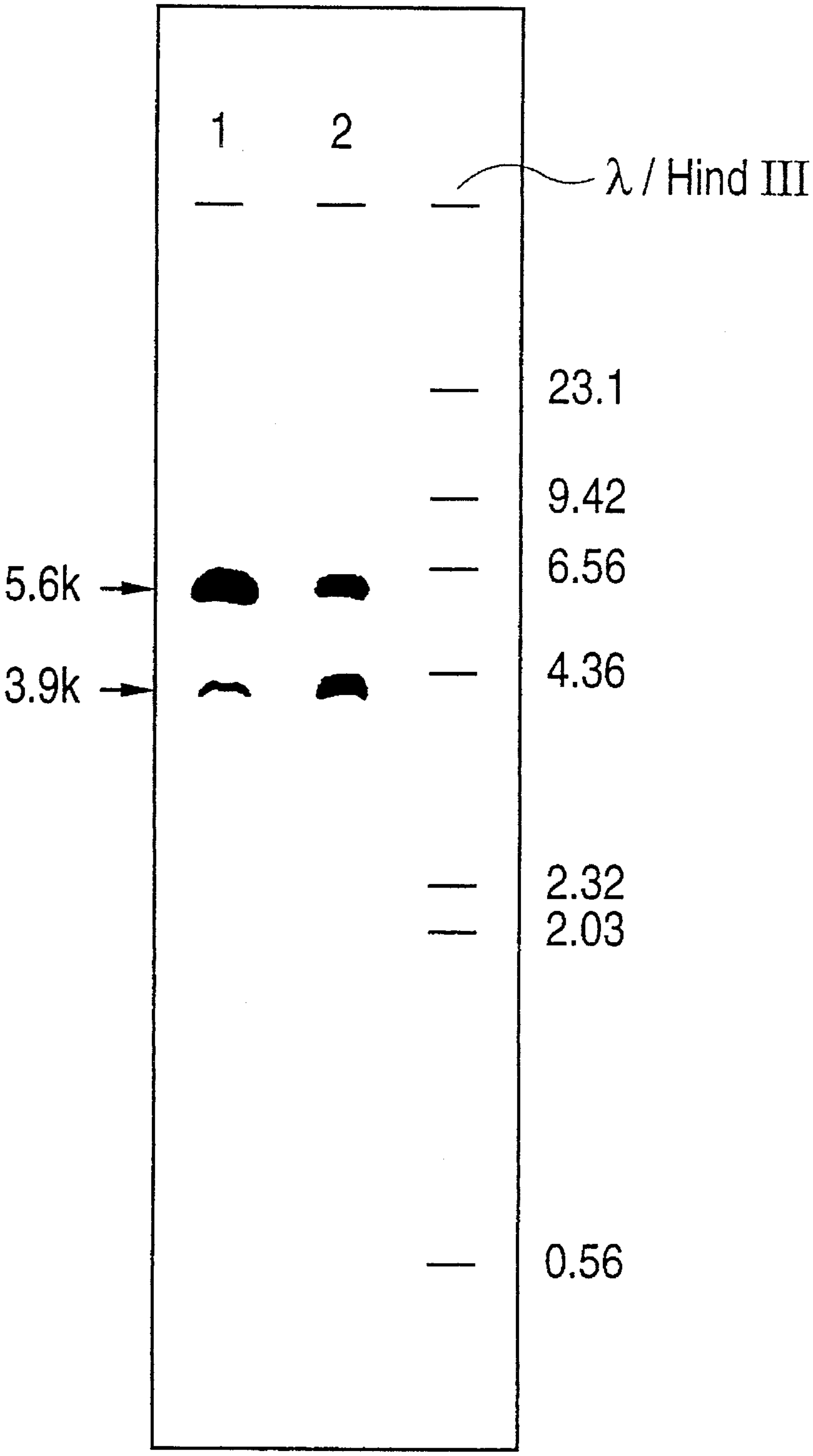
FIG. 10 is an illustration showing results of Southern hybridization which was conducted on the digestion product of DNAs extracted from CEF infected with K-A3VL with the restriction enzyme EcoRI using LacZ gene (lane 1) and KA3 fragment (lane 2) as a probe.

In order to confirm the position of the inserted LacZ gene, DNA extracted from CEF infected with K-A3VL was digested with EcoRI and the obtained fragments were subjected to the Southern hybridization (FIG. 10). Using the KA3 fragment and the LacZ gene as the probe, only bands of an expected size were detected in both probes of KA3 fragment (lane 2) and F gene (lane 1), and thereby it was confirmed that the incorporation of the LacZ gene was made by the homologous recombination and the recombinant virus was purified. The plaque of K-A3VL was smaller than that of the parent virus before the recombination and the growth of the obtained virus was apparently inhibited.

EXAMPLE 7

Figure 11A:
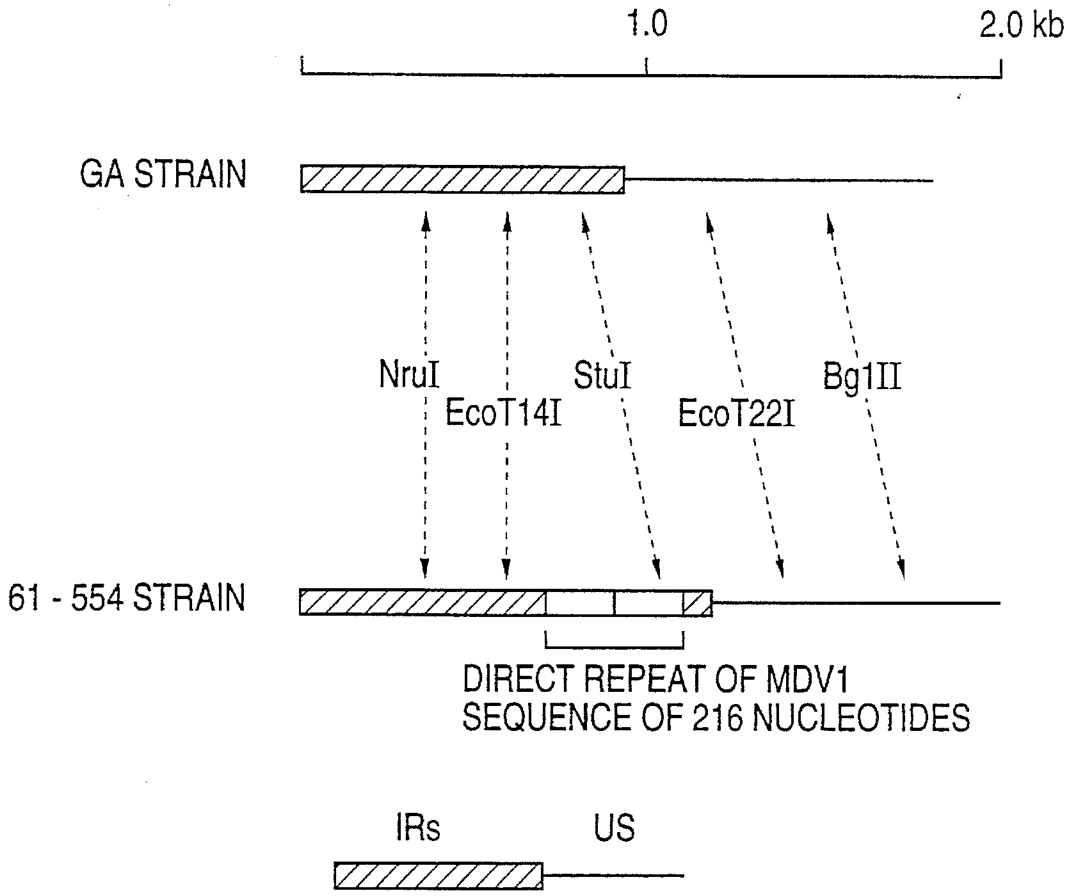
FIG. 11*a* shows a position of the repeat sequence in the A5 fragment of 61-554 strain.
Figure 11B:
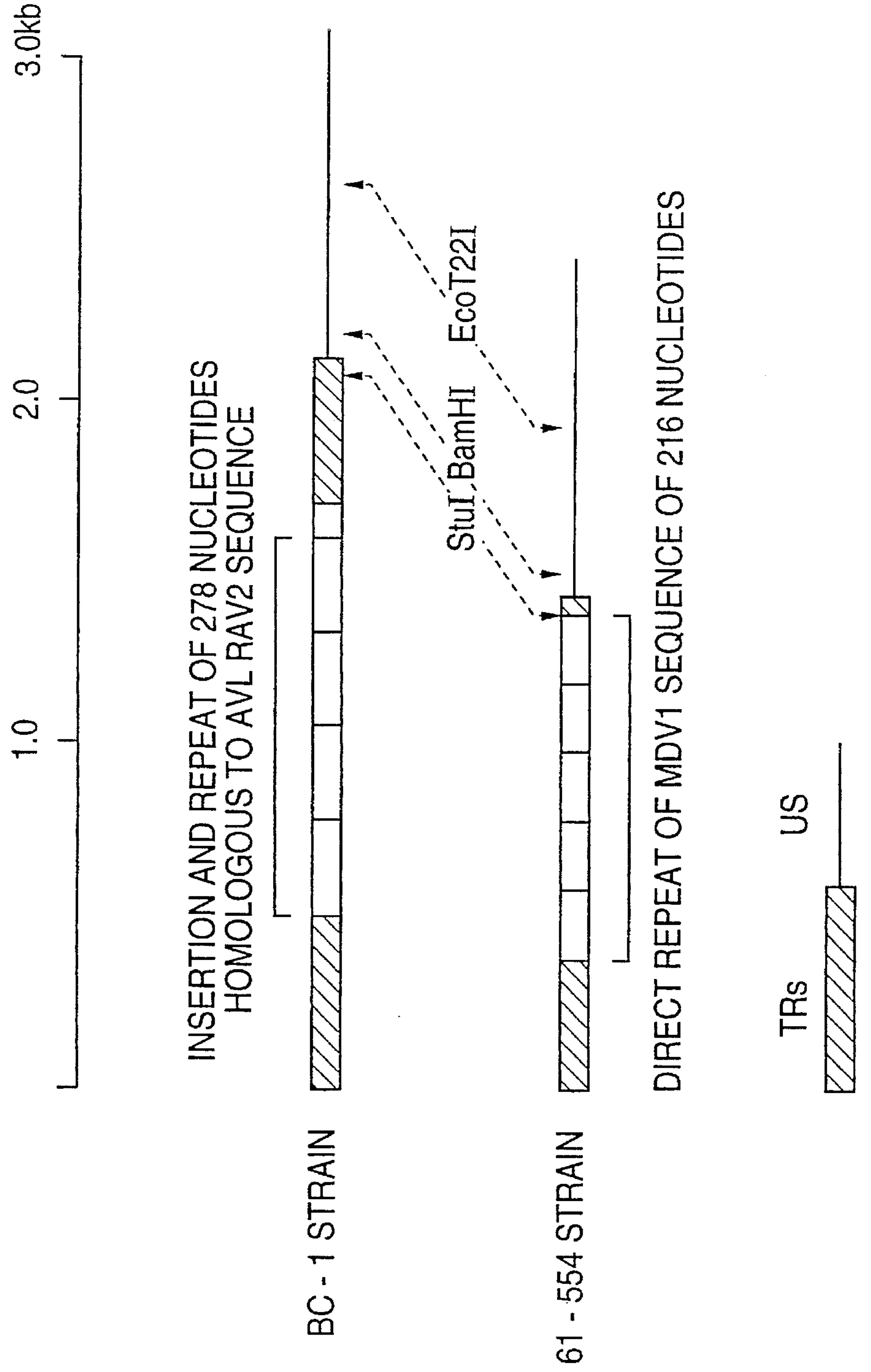
FIG. 11*b* shows a position of the repeat sequence in the A6 fragment of 61-554 and BC-1 strains.

(Determination of nucleotide sequence of repeated sequence in IRs and TRs)

pKA5 was digested with StuI and the obtained fragment of about 220 b was inserted into the SmaI site of pUC119 and the nucleotide sequence was determined. The obtained sequence was compared with the nucleotide sequence of the GA strain (GenBank Accession Number M80595, M. Sakaguchi). As a result, it was found that the region of the nucleotide numbers 614 to 822 was repeated twice (FIG. 11*a*). On the other hand, as the result of the determination of the nucleotide sequence of pKA6, said sequence was repeated 5 times (FIG. 11*b*).

The nucleotide sequence of a fragment of Marek's disease virus type I BC-1 strain corresponding to A6 was also determined. As a result, it was confirmed that 278 nucleotides having 88% homology to the DNA of avian leukemia virus (ALV RAV2) were inserted into the inverted repeat sequence TRs and the insertion was repeated 3.5 times (FIG. 11*b*). FIGS. 12A and 12B show the nucleotide sequence of the A6 fragment of the BC-1 strain.

From the above results, it was found that the inverted repeat sequences IRs and TRs adjacent to the Us region contains a region where a gene can be inserted without affecting the growth of the virus.

EXAMPLE 8

(Preparation of a recombinant Marek's disease virus inserted with SV40-LacZ gene; K-A5SL)

Figure 13:
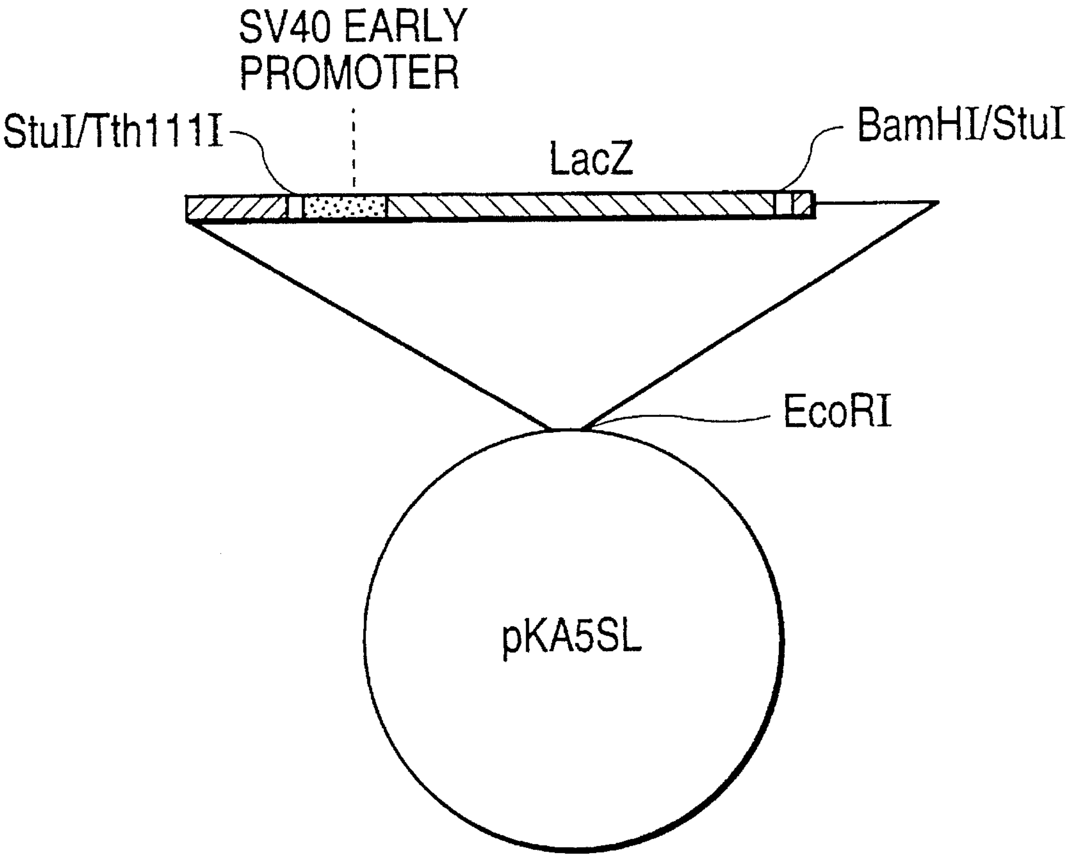
FIG. 13 shows the insertion plasmid pKA5SL.

Since the region where an exogenous gene can be inserted was confirmed in TRs and IRs adjacent to the Us region, an insertion plasmid was constructed using pKA5. pKA5 was digested with StuI to cut out repeated sequences of about 220 bp and the obtained fragments were subjected to an agarose gel electrophoresis. An fragment of 5.1 kb was taken out of the gel and dephosphated with alkali-phosphatase. Then, pCH110 (manufactured by Pharmacia, cat. No. 27-4508-01) was digested with BamHI and TthIII I and a fragment of 4.2 kb (SV40-LacZ) was obtained and blunt-ended. This fragment was inserted into the above dephosphated fragment to construct an insertion plasmid pKA5SL (FIG. 13).

The obtained plasmid was linearized by digestion with KpnI and then the recombination was carried out in accordance with the procedure for preparing the recombinant virus. The purified recombinant virus showed an excellent growth in vitro equivallent to the parent strain.

EXAMPLE 9

(Determination of nucleotide sequence of KA4)

pKA4 was digested with BalI and SmaI to give two fragments of 1.1 kb and of 4.9 kb, each of which was collected. The fragment of 1.1 kb was again inserted into the SmaI site of Δpuc119. The fragment of 4.9 kb was self-ligated and then single-stranded in accordance with the determination of nucleotide sequence and the nucleotide sequence was determined. The results are shown in FIG. 14. There was ORF of 639 nucleotides (Us639) in this sequence.

EXAMPLE 10

(Cloning of a K-A4BL that yields cell free type viruses)

After seeding CEF infected with K-A4BL ($1\times10^5$ PFU) and primary CEF ($3\times10^7$) into Petri dish of 10 cm diameter, the supernatant was harvested four days later when CPE was strongly shown. After centrifugation at 1500 rpm for 10 minutes (KN-30F manufactured by KUBOTA), pH of the supernatant was adjusted approximately to 7.4 with 0.7% sodium bicarbonate solution and added primary CEF ($3\times10^7$) and 5% BS. The mixture was cultured in Petri dish of 10 cm diameter. When the CPE was shown, the supernatant was harvested again and cultured in the same manner. After five time repeats of this manipulation, the supernatant was diluted ten folds with E-MEM supplemented 5% BS and added 2nd CEF ($5\times10^5$). Then, the mixture was seeded by 100 µl to every well of a 96 well plate and cultured. The cells of wells in which single plaque was shown were harvested five days later and seeded to Petri dish of 5 cm diameter with primary CEF ($1\times10^7$). The supernatant of the Petri dish was diluted and seeded to 96 well plates, then the supernatant of the well in which single plaque was shown was seeded to 96 well plate again. This manipulation was repeated for three times, then the cells of the wells in which single plaque was shown were harvested as virus stocks that produce high level of cell free viruses. In the supernatant of CEF cultured for five days after inoculation of this clone ($5\times10^4$ PFU), cell free type of LacZ(+) virus was yielded at levels of 200–500 PFU/ml. On the other hand, in the supernatant of CEF infected with a vaccine virus CVI988 which was cultured under the same conditions, cell free type of LacZ(+) virus was produced at levels of only 2–10 PFU/ml. The efficiency of homologous recombinantion is usually said 0.1% or so. Therefore, it has firstly become possible to effeciently prepare a recombinant virus by using K-A4BL as a parent strain which yields the cell free type of LacZ(+) virus at levels of 200–500 PFU/ml.

What is claimed is:

1. A recombinant Marek's disease virus type I produced by incorporating an exogenous gene expression cassette into a region of DNA extending from nucleotide no. 120 to nucleotide no. 758 of the DNA of SEQ ID NO:2, wherein said cassette comprises an exogenous gene and a promoter derived from an animal cell or an animal virus operably linked to said exogenous gene.

2. A process for preparing a recombinant Marek's disease virus type I which comprises (1) incorporating an exogenous gene expression cassette into a gene fragment derived from the Us region of Marek's disease virus type I genome, said gene fragment having a DNA sequence of SEQ ID NO: 2, said cassette comprising an exogenous gene and a promoter derived from an animal cell or an animal virus operably linked to said exogenous gene, and (2) incorporating the thus obtained recombinant gene fragment into the Marek's disease virus type I genome to effect the incorporation of said exogenous gene into a region of DNA extending from nucleotide no. 120 to nucleotide no. 758 of the DNA of SEQ ID NO:2 of the Marek's disease virus genome.

3. The process of claim 2 wherein said exogenous gene expression cassette is incorporated at the BalI restriction site between nucleotides nos. 121 and 122 of the DNA sequence of SEQ ID NO: 2.

4. A multivalent live vaccine for birds which comprises a recombinant Marek's disease virus type I produced by incorporating an exogenous gene expression cassette into a region of DNA extending from nucleotide no. 120 to nucleotide no. 758 of the DNA of SEQ ID NO:2, said cassette comprising an exogenous gene coding for a vaccine antigen and a promoter derived from an animal cell or an animal virus operably linked to said exogenous gene.

5. The live vaccine of claim 4 which is a vaccine for a chick.

6. The live vaccine of claim 4 wherein said exogenous gene coding for a vaccine antigen is a gene coding for an antigen of a Newcastle disease virus.

7. The live vaccine of claim 6 wherein said gene coding for an antigen of the Newcastle disease virus is a gene derived from an attenuated Newcastle disease virus.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3001 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Marek's disease gammaherpesvirus
( B ) STRAIN: 61-554 and BC-1

( x i ) SEQUENCE DESCRIPTION: SEQ ID NO:1:

```
GAATTCCTTC CTTTAAAATG AAAGATGTCC AGGTAGACGA TGCGGGATTG TATGTGGTTG   60
TGGCTTTATA TAATGGACGT CCAAGTGCAT GGACTTACAT TTATTTGTCA ACCGGTGAAA  120
CACTATCNTT AAATGTGGAA TGTATATGAA AACTACCACA AGCCGGGATT TGGGTATAAA  180
TCATTTCTAC AGAACAGTAG TATCATCGAC GAAAATGAGG CTAGCGATTG GTCCAGCTCG  240
TCCATTAAAC GGAGAAATAA TGGTACTATC CTTTATGATA TTTTACTCAC ATCGCTATCA  300
ATTGGGGCGA TTATTATCGT CATAGTAGGG GGTGTTTGTA TTGCCATATT AATTAGGCGT  360
AGGAGACGAC GTCGCACGCG GGGGTTATTC GATGAATATC CCAAATATAT GACGCTACCA  420
GGAAACGATC TGGGGGGCAT GAATGTTCCG TATGATAATG CATGCTCTGG TAACCAAGTT  480
GAATATTATC AAGAAAAGTC GGATAAAATG AAAAGAATGG GTTCGGGTTA TACCGCTTGG  540
CTAAAAAATG ATATNCCGAA ATTNGNAACC CCTAGATTTA ATCCCACTGA TATGNACANA  600
TTTAAACTTA ATGGGATATA GTATATGGAC GTCTATATGA CGAGAGTAAA TAAACTGACA  660
CTGCAAATGA AGCTGATCTA TATTGTGCTT TATATTGGGA CAAACCACTC GCACAAGCTC  720
ATTCAACACA TCCACTCTTG GACAGCTTCA TGTTAAAATA AACTGTAAAT CATTCAATGA  780
TAATGGGAGA AGAATGTGAG CAAGGATCCA TGGTGTCTGC TTTTTATAGT ATCTACCGCA  840
ATGCTACATA TAAAATAAAA ATATACCTCT ACCCAAAAAT GGGCGGTATG AGATGCACGG  900
GGAAAATACG CAGCTGTTCT CATATCCCCT GAACCGTACT CTTTTTCCCC TCTCCGCCCC  960
GCGGACCCCG AGGCCTCGTG GGGCACCTAT TTGCGCGGAG GAAGGCACGG TTCCTTTTTT 1020
TTTTGGGGGG GGGGGACCCA TCTGCGTAGA NAAAGGCACG GTTCCTCTTT TTTTTTTCCT 1080
ACAACATCTC GTTTGCATAT GCAAGCTCTG AGAACTTCCC TCTACCTCAA AGCGCCGTAG 1140
```

-continued

GGAACTGAGG TCTAATATTC AATCCTAGGC CACTCGCCAA TATAAGAGGG ACTTCCCCCC 1200

GCCTATAGAG AGAGGCAGCC CGAAAATGGA GCAGTGTAAA GCAGTACATG GGTGGTGGTA 1260

TGAAACTTGC GAATCGGGCT GTAACGGGGC AAGGCTTGAC TGAGGGGACC ATAGTATGTA 1320

TAGGCNAAAG GCGGGGCTTC GGTTGTANGC GGTTAGGAGT CCCCTCAGGA TACAGTAGTT 1380

GCGCTTTTGC ATAGGGAGGG GGAAATGTAG TCAAATAGAG CCAGAGGCAA CTTGAATAGC 1440

CTAAAGACCA AATAAGGAAA AAGCAAGACA TTCCATATGC TCATTGGTGG CGACTAGATA 1500

AGGAAGGAAT GACGCAAGGA CATATGGGCG TAGACGAAGC TATGTACGAT TATATAAGCT 1560

GTTGCCACCA TCAAAATAAA ACGCCATTTT ACCATTCACC ACATTGGTGT GCACCTGGGT 1620

AGATGGACAG ACCGTTGAGT CCCTAACGAT TGCGAACACC TGAATGAAGC AGAAGGCTTC 1680

ATTAATGTAG TCAAATAGAG CCAGAGGCAA CTTGAATAGC CTAAAGACCA AATAAGGAAA 1740

AAGCAAGACA TTCCATATGC TCATTGGTGG CGACTAGATA AGGAAGGAAT GACGCAAGGA 1800

CATATGGGCG TAGACGAAGC TATGTACGAT TATATAAGCT GTTCCACCAT CAAATAAACG 1860

CCATTTTACC ATTCACCACA TTGGTGTGCA CCTGGGTAGA TGGACAGACC GTTGAGTCCC 1920

TAACGATTGC CAACACCTGA ATGAAGGAGA AGGCCTCATT AATGTAGTCA AATAGAGCCA 1980

GAGGCAACTT GAATAGCCTA AAGACCAAAT AAGGGAAAAG CAAGACATTC CATATGCTCA 2040

TTGGTGGCGA CTAGATAAGG AAGGAATGAC GCAAGGACAT ATGGGCGTAG ACGAAGCTAT 2100

GTACGATTAT ATAAGCTGTT GCCACCATCA AATAAACGCC ATTTTACCAT TCACCACATT 2160

GGTGTGCACC TGGGTAGATG GACAGACCGN TGAGTCCCTN ACGATTGCGN ACACCTNAAT 2220

GAAGNNGAAG GCCTCATTAA TGNAGTCAAA TAGAGCCAGA GGCTAACTTG AATAGCCTAA 2280

AGGACCAAAT AAGGAAAAAG CAAGACATTC CATATGCTCA TTGGTGGCGA CTAGATAAGG 2340

AAGGAATGAC GCAAGGACAT ATGGGCGTAG ACGAAGCTAT GTACGATTAT ATAAGCTAAA 2400

CCCAGGAGAC ACGCTGTGGT TAGCTCGTCG ATTCAGTATC CCCCCCNAAN GGCCCCCCCT 2460

TTTTNGGCCC CNGGTTTNCC NNAANCNTTG NCCAAAAANC CTAGCCCAAA AGCNNCGTAA 2520

NNCTTGGGAT NNTAAAAAAA ANGGAGAACN CGTAAGGCCA AAAAANCTAT TTTAATGGGT 2580

CCCCGACAAA NATAAACACA CTCCCCCCTC CCCCTTNCCC CTGTTCAAGT CAGNAAACCC 2640

GTCGNAAGAT TAATTCTCAA AATCCCAATN CGGCGAGCAT GTAAGACCCC GGCCAATCGT 2700

ACAGAACCCC GAGTTTTGTT TACTTGCAGA TATGCACCGC CCTTCCTTGA CGTGNCAAAC 2760

AAACTAAGCT GTGTTTATAT AAAACGGCAC CCNACCCATA TACTCGTATA CTTGTACGAA 2820

CCAGTGGTTT TTTTATGTGG GGGAGGGAGA AGGACAAATT AAAACATTGN ACTTGCCTGG 2880

GCTACAATTC CCTTTTGGCT CGAGCTATGT CGGAGAGTNC CGGTGGACCC GNGGTTGTGC 2940

TTTGGGCTGA AGGAANTCGA GNTNGGTACC CGGGGANCCT CTAGAGTCGA CCCTGAAAGC 3000

T 3001

( 2 ) INFORMATION FOR SEQ ID NO:2:

( i ) SEQUENCE CHARACTERISTICS:

( A ) LENGTH: 900 base pairs ( B ) TYPE: nucleic acid ( C ) STRANDEDNESS: single ( D ) TOPOLOGY: linear ( i i ) MOLECULE TYPE: DNA (genomic)

( v i ) ORIGINAL SOURCE:

( A ) ORGANISM: Marek's disease gammaherpesvirus ( B ) STRAIN: 61-554

( x i ) SEQUENCE DESCRIPTION: SEQ ID NO:2:

-continued

| | | | | | | |
|---|---|---|---|---|---|---|
| TGTTGCCTTT | TTGTTGTATA | TGAAGATATT | TAATGTGGCG | TTGAGCCTAA | TGAGAGGAGA | 60 |
| ACGTGTTTGA | ACACTGGAGA | CGAGCGCCGT | GTAAGATTAA | AACATATTGG | AGAGGTATGG | 120 |
| CCATGTGGTC | TCTACGGCGC | AAATCTAGCA | GGAGTGTGCA | ACTCCGGGTA | GATTCTCCAA | 180 |
| AAGAACAGAG | TTATGATATA | CTTTCTGCCG | GCGGGGAACA | TGTTGCGCTA | TTGCCTAAAT | 240 |
| CTGTACGCAG | TCTAGCCAGG | ACCATATTAA | CCGCCGCTAC | GATCTCCCAG | GCTGCTATGA | 300 |
| AAGCTGGAAA | ACCACCATCG | TCTCGTTTGT | GGGGTGAGAT | ATTCGACAGA | ATGACTGTCA | 360 |
| CGCTTAACGA | ATATGATATT | TCTGCTTCGC | CATTCCACCC | GACAGACCCG | ACGAGAAAAA | 420 |
| TTGTAGGCCG | GGCTTTACGG | TGTATTGAAC | GTGCTCCTCT | TACACACGAA | GAAATGGACA | 480 |
| CTCGGTTTAC | TATCATGATG | TATTGGTGTT | GTCTTGGACA | TGCTGGATAC | TGTACTGTTT | 540 |
| CGCGCTTATA | TGAGAAGAAT | GTCCGTCTTA | TGGACATAGT | AGGTTCGGCA | ACGGGCTGTG | 600 |
| GAATAAGTCC | ACTCCCCGAA | ATAGAGTCTT | ATTGGAAACC | TTTATGTCGT | GCCGTCGCTA | 660 |
| CTAAGGGGAA | TGCAGCAATC | GGTGATGATG | CTGAATTGGC | ACATTATCTG | ACAAATCTTC | 720 |
| GGGAATCGCC | AACAGGAGAC | GGGGAATCCT | ACTTATAACT | AATCGCACAA | TTATTAATAG | 780 |
| GATTTTAGGA | AAAACTGCTA | CTAACGTTGT | TTAAATAATA | AAATTTTATT | TTCAATAAGG | 840 |
| CATTACAGTG | TTGTCATGAT | TGTATGTATT | ATATGGGGTA | TGCATGAGGA | TTACTTCGAT | 900 |